US010514413B2

(12) United States Patent
Cibula et al.

(10) Patent No.: US 10,514,413 B2
(45) Date of Patent: Dec. 24, 2019

(54) ESTIMATION OF ARC LOCATION IN THREE DIMENSIONS

(71) Applicant: KW Associates LLC, Corvallis, OR (US)

(72) Inventors: Matthew A. Cibula, Salem, OR (US); Paul E. King, Albany, OR (US); C. Rigel Woodside, Corvallis, OR (US)

(73) Assignee: KW Associates LLC, Corvallis, OR (US)

( * ) Notice: Subject to any disclaimer, the term of this patent is extended or adjusted under 35 U.S.C. 154(b) by 163 days.

(21) Appl. No.: 15/715,018

(22) Filed: Sep. 25, 2017

(65) Prior Publication Data

US 2018/0088164 A1 Mar. 29, 2018

Related U.S. Application Data

(60) Provisional application No. 62/400,018, filed on Sep. 26, 2016.

(51) Int. Cl.
*G01R 31/02* (2006.01)
*C21C 5/52* (2006.01)
(Continued)

(52) U.S. Cl.
CPC .......... *G01R 31/024* (2013.01); *G01N 27/82* (2013.01); *G01R 31/08* (2013.01)

(58) Field of Classification Search
CPC .. G01R 31/024; G01R 31/08; G01R 33/0064; G01R 33/10
See application file for complete search history.

(56) References Cited

U.S. PATENT DOCUMENTS 2,727,936 A 12/1955 Boyer
2,727,937 A 12/1955 Boyer
(Continued)

FOREIGN PATENT DOCUMENTS

JP S60-077939 5/1985
JP H03-274382 12/1991

OTHER PUBLICATIONS

Co-owned U.S. Appl. No. 16/209,943 entitled "Sensing & control of position of an electrical discharge" filed Dec. 4, 2018 in the names of Cibula et al (available in IFW).
(Continued)

*Primary Examiner* — Dominic E Hawkins
(74) *Attorney, Agent, or Firm* — David S. Alavi

(57) ABSTRACT

Multiple magnetic field sensors are arranged around a current-containing volume at multiple longitudinal and circumferential positions. Each sensor measures multiple magnetic field components and is characterized by one or more calibration parameters. A longitudinal primary current flows through two end-to-end electrical conductors that are separated by an arc gap, and flows as at least one longitudinal primary electric arc that spans the arc gap and that moves transversely within the arc gap. Estimated transverse position of the primary electric arc is calculated, based on the longitudinal position of the arc gap, and two or more of the measured magnetic field components along with one or more corresponding sensor positions or calibration parameters. In addition, estimated occurrence, position, and magnitude of a transverse secondary current (i.e., a side arc) can be calculated based on those quantities.

34 Claims, 9 Drawing Sheets

(51) Int. Cl.
  *G01N 27/82* (2006.01)
  *G01R 31/08* (2006.01)

(56) References Cited

U.S. PATENT DOCUMENTS

| | | | |
|---|---|---|---|
| 2,951,890 A | 9/1960 | Yeomans et al. | |
| 2,972,695 A | 2/1961 | Wroe | |
| 2,978,525 A | 4/1961 | Gruber et al. | |
| 3,398,229 A | 8/1968 | De Corso | |
| 3,546,348 A | 12/1970 | De Corso | |
| 3,628,948 A | 12/1971 | Bruning | |
| 3,680,163 A | 8/1972 | De Corso | |
| 3,708,279 A | 1/1973 | De Corso | |
| 4,122,292 A | 10/1978 | Karinsky | |
| 4,495,625 A | 1/1985 | Heberlein et al. | |
| 4,581,745 A | 4/1986 | Mathews et al. | |
| 4,762,165 A | 8/1988 | Ogino et al. | |
| 5,206,596 A * | 4/1993 | Beihoff | H02H 1/0015 324/536 |
| 5,373,529 A | 12/1994 | Zanner et al. | |
| 6,605,936 B1 * | 8/2003 | Tamai | G01R 15/202 324/117 R |
| 8,111,059 B1 | 2/2012 | King et al. | |
| 2006/0012369 A1 * | 1/2006 | Neufeld | G01R 33/34046 324/318 |
| 2011/0221437 A1 * | 9/2011 | Stockum | G01R 33/072 324/252 |
| 2013/0092208 A1 * | 4/2013 | Robbins | H01L 31/02021 136/244 |
| 2013/0226479 A1 * | 8/2013 | Grosjean | G01R 31/024 702/58 |
| 2014/0015520 A1 * | 1/2014 | Kunjappan | G01D 5/145 324/207.14 |

OTHER PUBLICATIONS

International Search Report dated Dec. 12, 2017 in counterpart App No. PCT/2017/053326.

Zanner et al; On the Origin of Defects in VAR Ingots; International Symposium on Liquid Metal Processing and Casting, Santa Fe, NM, USA, p. 13 (2005).

Zanner et al; Observations of melt rate as a function of . . . during vacuum consumable arc remelting of . . . ; Metallurgical & Materials Transactions B v15 p. 117 (1984).

Woodside; Investigating arc behavior in a DC vacuum arc remelting furnace using magnetic flux density measurements: masters thesis, Oregon State University: (2008).

Woodside; Arc Distribution and Motion During the Vacuum Arc Remelting Process As Detected with a Magnetostatic Approach; PhD dissertation, Oregon State University (2010).

Woodside et al; A Measurement System for Determining the Positions of Arcs During Vacuum Arc Remelting; IEEE Int'l Instrumentation & Measurement Tech Conf; p. 452 (2010).

Ward et al; Ensemble Arc Motion & Solidification During the Vacuum Arc Remelting of a Nickel-based Superalloy; Int'l Symp on Liquid Metal Processing & Casting; p. 49 (2005).

Woodside et al: Characterizing Arc Motion and Distribution During Vacuum Arc Remelting; nt'l Symp on Liquid Metal Processing & Casting; v75 (2009).

Woodside et al; Arc Distribution During the Vacuum Arc Remelting of Ti—6Al—4V; Metallurgical & Materials Transactions B v44 n1 p. 154 (2012).

* cited by examiner

FIG. 9A
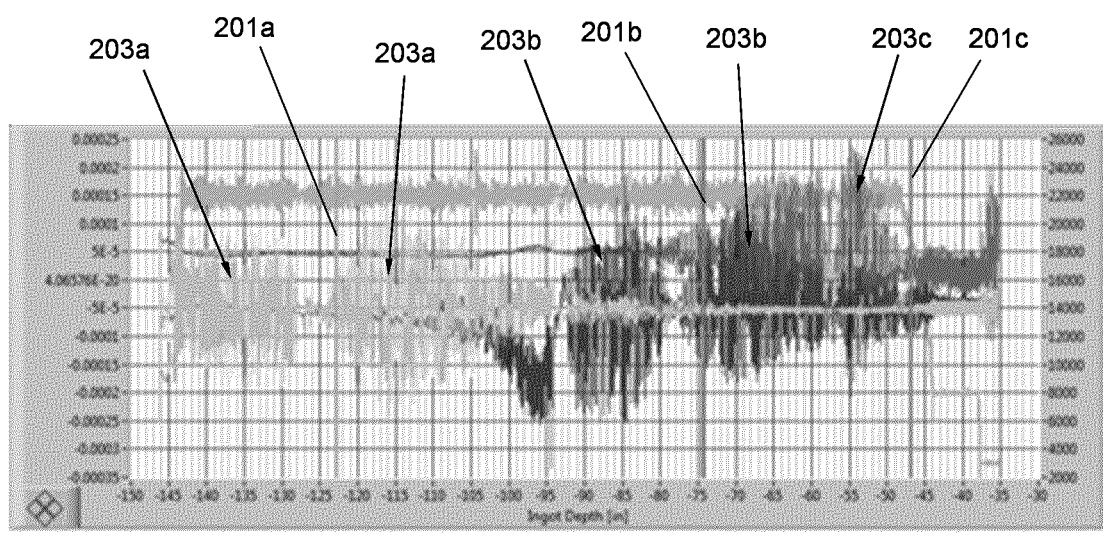
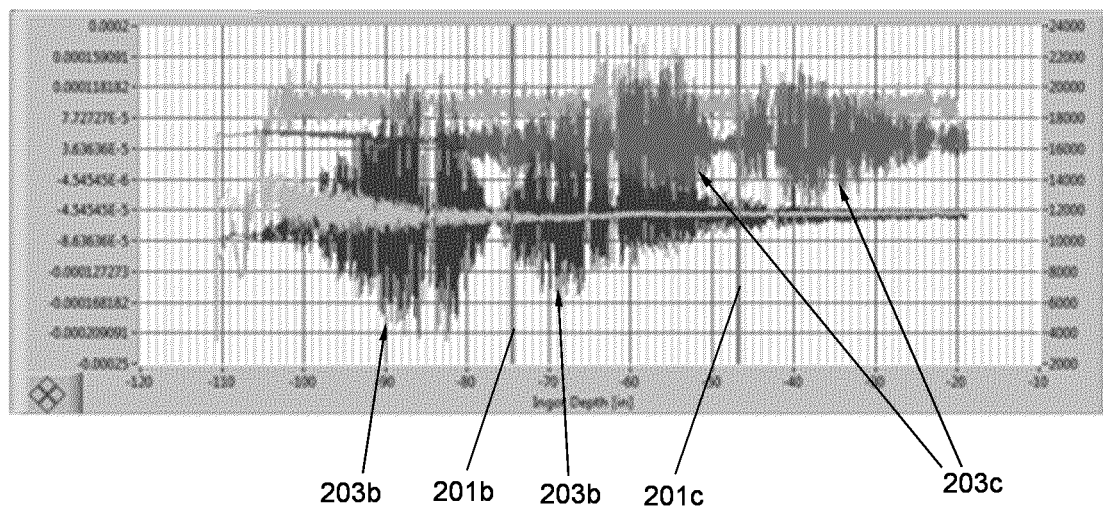
FIG. 9B

ESTIMATION OF ARC LOCATION IN THREE DIMENSIONS

BENEFIT CLAIM TO RELATED APPLICATION

This application claims benefit of U.S. provisional App. No. 62/400,018 filed Sep. 26, 2016 in the names Matthew A. Cibula, Paul E. King, and C. Rigel Woodside, said provisional application being hereby incorporated by reference as if fully set forth herein.

FIELD OF THE INVENTION

The field of the present invention relates to electric arcs. In particular, apparatus and methods are disclosed for estimating the location of an electric arc in three dimensions.

SUMMARY

An inventive apparatus comprises a set of multiple magnetic field sensors, a data acquisition system operatively coupled to the magnetic field sensors, and a computer system operatively coupled to the data acquisition system. The multiple magnetic field sensors are arranged around a lateral periphery of a current-containing volume into which an input current flows and through which a primary electric current flows in a predominantly longitudinal direction. The primary current flows through first and second longitudinal electrical conductors positioned end-to-end within the current-containing volume and separated by an arc gap, and flows as one or more primary electric arcs spanning the arc gap and movable in two transverse dimensions within the arc gap between the first and second conductors. Each sensor of the set is positioned at a corresponding one of multiple distinct sensor positions; the sensor positions are arranged among two or more distinct longitudinal positions along the current-containing volume and among two or more distinct circumferential positions around the lateral periphery of the current-containing volume. Each sensor of the set is arranged so as to measure magnetic field components in two or more spatial dimensions; each sensor of the set is characterized by one or more corresponding calibration parameters. The data acquisition system is structured and connected so as to convey to the computer system signals from the multiple sensors indicative of the measured magnetic field components. The computer system (comprising one or more electronic processors and one or more digital storage media coupled thereto) is structured, connected, and programmed so as to calculate an estimated transverse position of the one or more primary electric arcs within the arc gap. The calculation is based at least in part on an estimated longitudinal position of the arc gap, and two or more of the measured magnetic field components along with one or more corresponding sensor positions or calibration parameters. The current-containing volume can be enclosed within an electrically conductive chamber that defines the lateral periphery of the current-containing volume, and the multiple sensor positions can be located outside the chamber. The chamber can comprise an electric arc furnace, the first conductor can comprise an electrode of the furnace, the second conductor can comprise an ingot formed within the furnace, and the furnace can be arranged so that the arc gap moves longitudinally through the furnace as the input current flows during a melt period, causing the electrode to melt and shrink and the ingot to grow.

An inventive method, for estimating the transverse position of the one or more primary electric arcs as a function of longitudinal position of the arc gap within the electric arc furnace during the melt period, comprises: (A) during the melt period, measuring the magnetic field components in two or more spatial dimensions using the set of multiple magnetic field sensors; (B) using the data acquisition system, conveying from the multiple sensors to the computer system the signals from the multiple sensors indicative of the corresponding measured magnetic field components; and (C) using the computer system, for each one of multiple melt times within the melt period, calculating the corresponding estimated transverse position of the one or more primary electric arcs within the arc gap. The calculation is based at least in part on the longitudinal position of the arc gap at the corresponding melt time, and two or more of the magnetic field components, measured at the corresponding melt time, along with one or more corresponding sensor positions or calibration parameters.

Objects and advantages pertaining to locating an electric arc may become apparent upon referring to the example embodiments illustrated in the drawings and disclosed in the following written description or appended claims, and shall fall within the scope of the present disclosure or appended claims.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIGS. 9A and 9B are schematic plots of measured magnetic field longitudinal components as a function of arc gap longitudinal position for three different senor rings in two different arc furnaces.

The embodiments depicted are shown only schematically: all features may not be shown in full detail or in proper proportion, certain features or structures may be exaggerated relative to others for clarity, and the drawings should not be regarded as being to scale. The embodiments shown are only examples: they should not be construed as limiting the scope of the present disclosure or appended claims.

DETAILED DESCRIPTION OF EMBODIMENTS

The subject matter disclosed herein may be related to that disclosed in U.S. Pat. No. 8,111,059 entitled "Electric current locator" issued Feb. 7, 2012 to King et al (hereinafter referred to as the '059 patent), said patent being incorporated by reference as if fully set forth herein.

Figure 1:
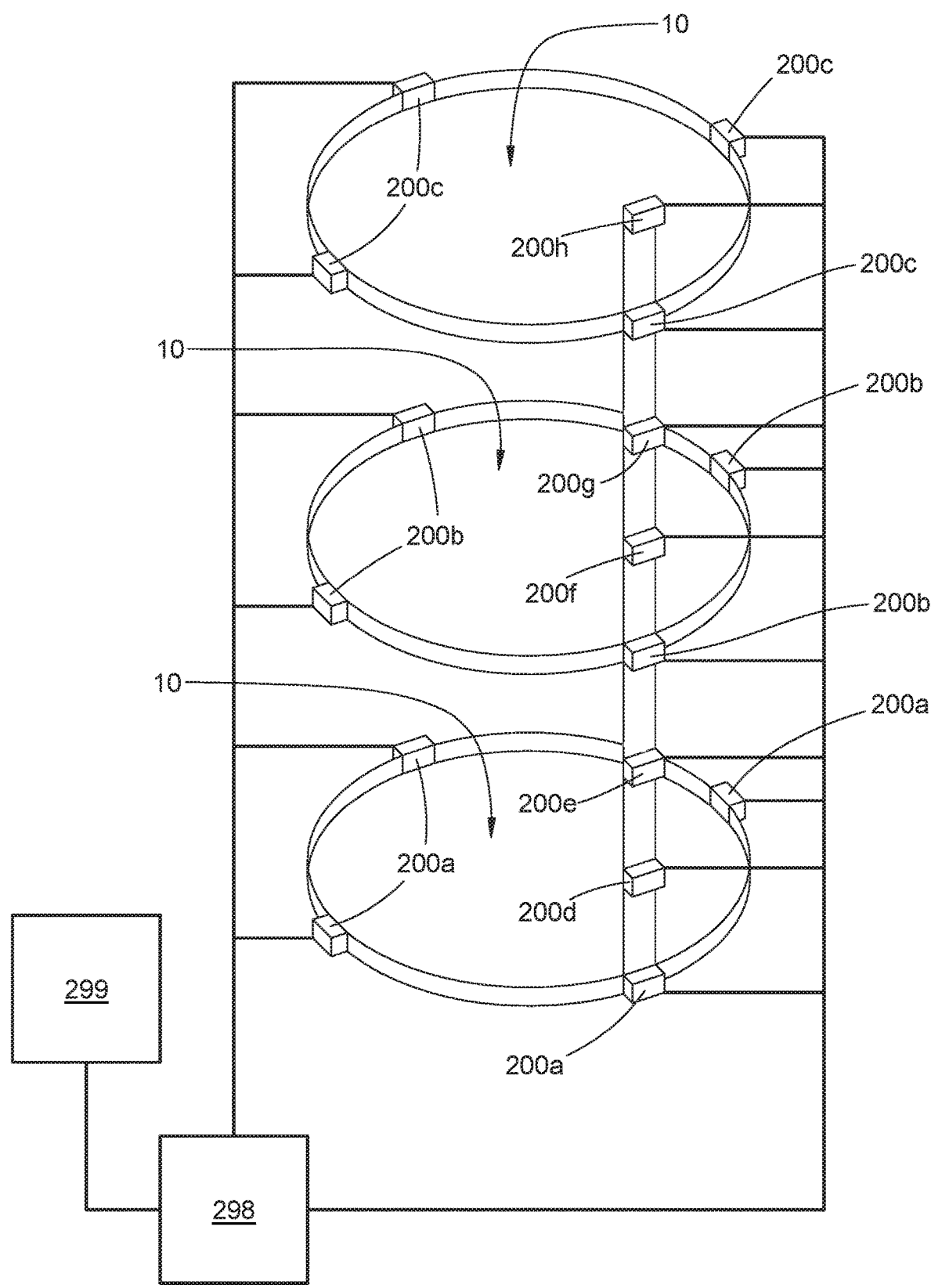
FIG. 1 is a schematic perspective view of an example inventive arrangement of magnetic sensors coupled to a computer system by a data acquisition system.
Figure 2:
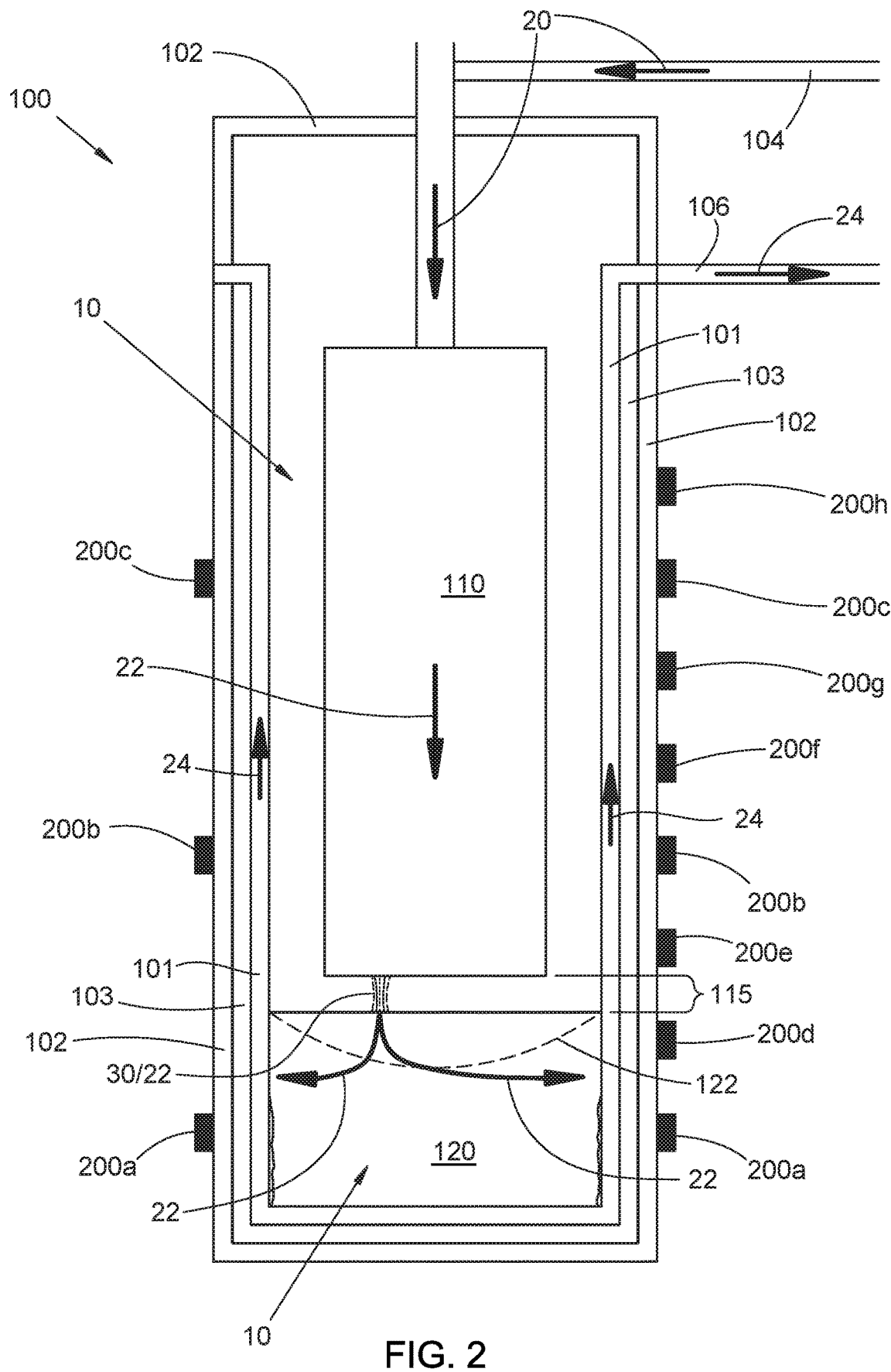
FIG. 2 is a schematic longitudinal cross section of an arc furnace with an example inventive arrangement of magnetic sensors, and with a primary electric current flowing as a primary electric arc.
Figure 3:
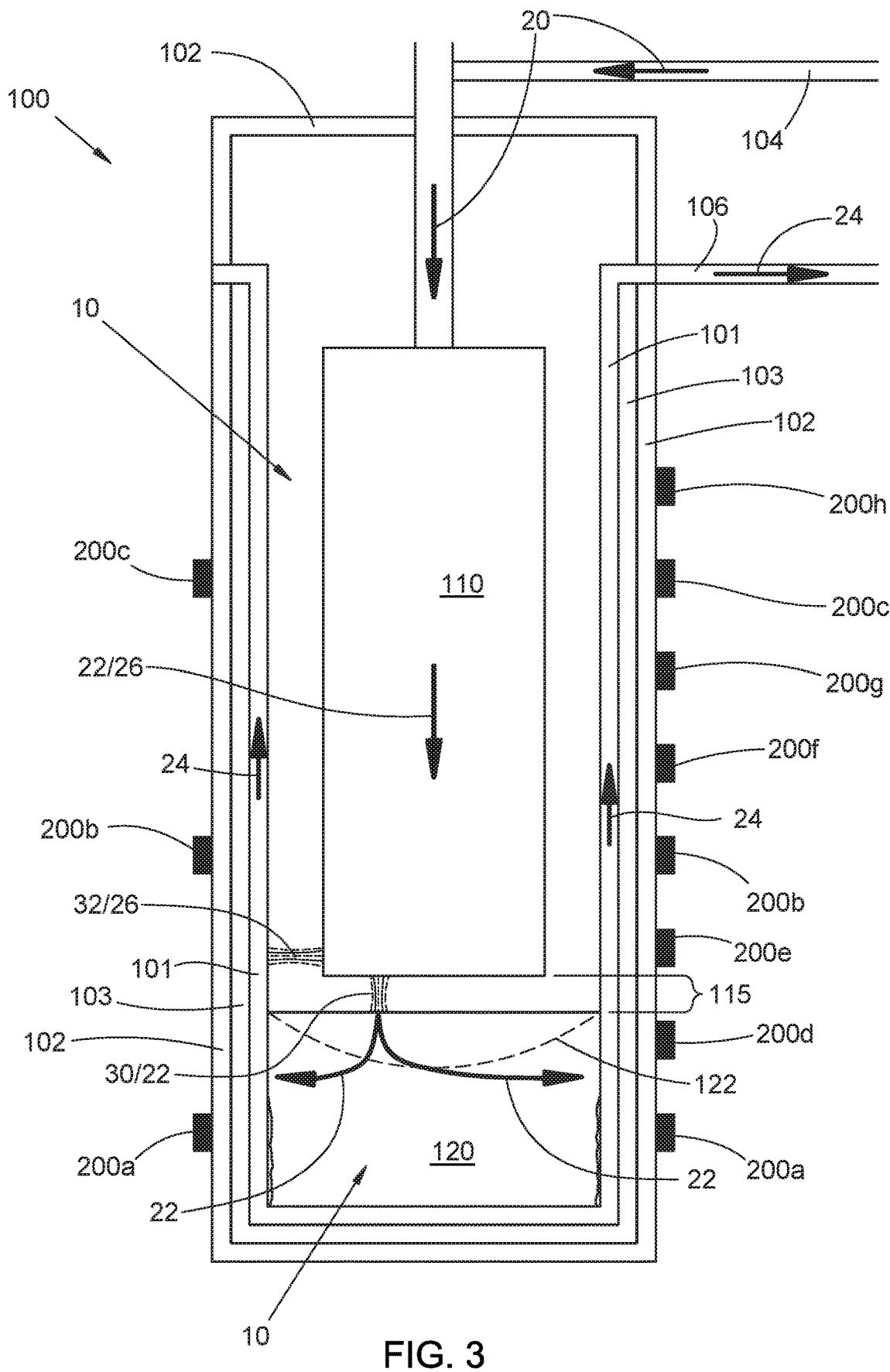
FIG. 3 is a schematic longitudinal cross section of the arc furnace with the example inventive arrangement of magnetic sensors, and with a primary electric current flowing as a primary electric arc and a secondary electric current flowing as a secondary electric arc.

An example of an inventive apparatus for estimating the location of an electric arc comprises a set of multiple magnetic field sensors 200, a data acquisition system 298 operatively coupled to the magnetic field sensors 200, and a computer system 299 operatively coupled to the data acquisition system (e.g., as in FIG. 1). In some instances disclosed herein the magnetic field sensors are referred to collectively or generically in the description, and indicated collectively or generically in the drawings, using the single reference number 200; in other instances herein the magnetic field sensors are referred to individually or as subsets in the description, and indicated individually or as subsets in the drawings, using references numbers 200a, 200b, 200c, and so on. FIGS. 1 through 3 illustrate schematically example arrangements of the multiple magnetic field sensors 200 around a lateral periphery of a current-containing volume 10. In some examples (e.g., as in FIGS. 2 and 3) the current-containing volume 10 is the interior volume of a chamber such as an electric arc furnace 100 and is bounded by its walls, which define the lateral periphery of the current-containing volume 10. "Around the lateral periphery" can denote sensor positions exactly on the lateral boundary of the current-containing volume, or sensor positions inside or outside that lateral boundary, provided that the sensor positions span multiple distinct circumferential positions relative to the current-containing volume 10. In many examples (e.g., as in FIGS. 2 and 3) the walls of the arc furnace 100 include an inner, electrically conductive crucible 101 (often made of copper), an outer wall 102, and a cooling water jacket 103 between them; in such examples the sensors 200 typically are positioned on the outer surface of the outer wall 102. Although such examples are the focus of the present disclosure, the apparatus and methods disclosed herein also can be employed for locating an electric arc within other types or arrangements of a current-carrying volume 10, while nevertheless remaining within the scope of the present disclosure or appended claims.

An input electric current 20 flows into the current-carrying volume 10; a portion of that input current flows within the current-carrying volume 10 as a primary electric current 22. In some instances the input current 20 and the primary current 22 are equal, i.e., all of the input current 20 flows within the current-carrying volume 10 as the primary current 22 (e.g., as in FIG. 2). In other instances the primary current 22 is less than the input current 20 (e.g., as in FIG. 3; discussed further below). The terms "longitudinal" and "transverse" as used herein are defined relative to the desired direction of flow of the primary current 22. A boundary of the current-containing volume 10 in a transverse direction is referred to as a lateral boundary or a lateral periphery. For examples in which the current-containing volume 10 is contained within an electric arc furnace 100, the long axis of the furnace 100 defines the longitudinal direction or dimension (e.g., vertical in FIGS. 2 and 3), and directions perpendicular to that furnace axis are the transverse directions or dimensions (e.g., horizontal in FIGS. 2 and 3); side walls of the arc furnace 100 define the lateral periphery of the current-containing volume 10 within the arc furnace 100. The longitudinal direction or dimension may in some instances be referred to as the z-direction or z-dimension, or as the vertical direction or dimension; in such instances the transverse directions or dimensions may be referred to as the x- and y-directions or x- and y-dimensions, or as the horizontal directions or dimensions. Those additional designations or descriptors are arbitrary, are made only for convenience of description, and should not be construed as limiting the scope of the present disclosure or appended claims.

First and second longitudinal electrical conductors 110 and 120, respectively, are positioned end-to-end within the current-containing volume 10 and are separated by an arc gap 115. In examples wherein the current-containing volume 10 is the interior of the arc furnace 100, the first longitudinal electrical conductor 110 can comprise the electrode 110 of the furnace 100, and the second longitudinal electrical conductor 120 can comprise the ingot 120 formed within the furnace 100. During operation of the furnace 100, the ingot 120 typically includes a pool of molten metal (i.e., the so-called melt pool 122) at its top surface (with the furnace 100 operated in its typical orientation, with its long axis oriented substantially vertically and with the electrode 110 positioned above the ingot 120). The primary current 22 flows through the first conductor 110, flows between the conductors 110/120 as one or more primary electric arcs 30 that span the arc gap 115, and flows through the second conductor 120. In the arc furnace example, the primary current 22 flows through the electrode 110, flows between the electrode 110 and the ingot 120 as one or more primary arcs 30 spanning the arc gap 115, and flows through at least a portion of the ingot 120. In the arc furnace example, the primary current 22 flows from the ingot 120 into the side walls of the crucible 101 and flows through at least portions of the crucible walls as a return current 24. It is typically assumed that the primary current 22 flows primarily from near the top of the ingot 120 into the side walls of the crucible 101 before flowing as the return current 24 (as in the drawings); it is also possible that at least a portion of the primary current 22 flows into the crucible walls elsewhere along the ingot 120, or at the bottom of the ingot 120, before flowing as the return current 24. The scope of the present disclosure and appended claims shall encompass each of those alternatives as well as any combination of one or more of those alternatives.

An electric arc furnace often is operated for the purpose of vacuum arc remelting, in which the electrode 110 is made of a high-value metal or alloy, and it is desired to improve the quality of the material (e.g., by improved homogeneity of macroscopic or microscopic structure or composition, by reduction of impurities, and so forth). Under vacuum conditions (e.g., less than about 1 mmHg or less than about 0.1 mmHg), a large electric current (e.g., several kiloamperes) is driven through the electrode 110 to strike an arc 30 against a small amount of seed material at the bottom of the crucible 101. The primary current 22 flowing as the primary electric arc 30 causes the electrode 110 to melt at the arc gap 115 and form a melt pool 122. Solidification of the melted material forms and grows the ingot 120. As the remelting process proceeds, the ingot 120 grows, the electrode 110 shrinks, and the arc gap 115 moves upward through the arc furnace 100. The water jacket 103 around the crucible 101 is employed to control the solidification rate and conditions to yield the desired properties of the ingot material. The electrode 110 has a smaller diameter then the crucible 101 (and hence the ingot 120 that is formed) to avoid current flow from the electrode 110 to the walls of the crucible 101. Because of this, the electrode 110 must be moved downward at the correct rate during operation of the furnace in order to maintain the correct height of the arc gap 115 (i.e., the distance between the electrode 110 and the ingot 120) as the electrode 110 melts away and the ingot 120 grows. An arc furnace 100 can be any suitable or desirable length; many examples are over 100 inches long, or over 200 inches long, or even longer.

The diameter of the electrode 110 typically is larger (usually much larger) than the transverse extent of the primary electric arc 30, thereby allowing the primary arc 30 to move in two transverse dimensions within the arc gap 115 between the electrode 110 and the ingot 120. Typical transverse dimensions of electrode 110 (e.g., the diameter of a cylindrical electrode 110) range from about 12 inches to about 36 inches or more; crucible transverse dimensions typically are about 2 to 4 inches larger than the electrode dimensions. The primary arc 30, on the other hand, typically is no more than a few millimeters wide, allowing the primary arc 30 to move relatively freely across the transverse dimensions of the arc gap 115. That transverse movement of the primary arc 30 can affect the quality of the material forming the ingot 120. It would be desirable to provide an estimate of the transverse position of the primary electric arc 30, as a function of longitudinal position along the ingot 120 (or equivalently, as a function of longitudinal position within the furnace 100 of the arc gap 115). Such an estimate of the primary arc's position can take a variety of forms and can be used for a variety of purposes. In some examples, a detailed trajectory of estimated positions of the primary arc 30 can be generated and stored; in other examples a distribution function can be generated that reflects the relative probability density that the primary arc 30 was at a particular transverse position; that density can be averaged over any suitable or desirable timescale, e.g., over 1 second, 10 seconds, 100 seconds, or other suitable interval. The estimated arc transverse position can be generated in real time as the furnace is operated, or can be generated later in so-called offline processing.

The set of multiple magnetic sensors 200 measure magnetic field components around the current-containing volume 10; those measured values are used to calculate an estimated position of the primary arc 30. Each magnetic sensor 200 is positioned at a corresponding one of multiple distinct sensor positions. The sensor positions are arranged among two or more distinct longitudinal positions along the current-containing volume and among two or more distinct circumferential positions around the lateral periphery of the current-containing volume 10 (e.g., as in FIGS. 1 through 3). This is in contrast to the arrangement of magnetic sensors disclosed in the '059 patent, in which all the magnetic sensors are arranged at a single longitudinal position along the current-containing volume 10. Each magnetic sensor 200 is arranged so as to measure magnetic field components in two or more spatial dimensions; in many examples the magnetic sensors measure magnetic field components in all three spatial dimensions. Each magnetic sensor 200 is characterized by one or more corresponding calibration parameters (discussed further below). The magnetic sensors 200 can be of any suitable type, e.g., Hall effect sensors or magnetoresistive sensors. Discrete devices can be used to measure each spatial component at a given sensor location, or multiple devices can be integrated into a single, monolithic sensor that measures two or three magnetic field components. In some examples, a single, integrated, 3D Hall effect sensor is located at each sensor position to measure the magnetic field components in all three spatial dimensions. The output of such sensors typically is a voltage proportional to the measured magnetic field component. In one specific example, sensors 200 can measure up to about 100 gauss with resolution of about 0.01 gauss.

The data acquisition system 298 can be of any suitable type or arrangement, and typically includes one or more analog-to-digital converters (A/Ds). The computer system 299 comprises one or more electronic processors and one or more digital storage media coupled to the one or more processors. The data acquisition system 298 is structured and connected so as to convey to the computer system 299 signals from the multiple sensors 200 indicative of the measured magnetic field components. In some examples, the data acquisition system can be a separate set of one or more components or modules coupling the sensors 200 to the computer system 299. In some examples, the data acquisition system 298 can be distributed among and integrated with the sensors 200 (e.g., by integration of one or more Hall sensors and one or more A/Ds on a single chip or in a single device at each sensor position). In some examples the data acquisition system can be integrated with the computer system 299 (e.g., by integration of one or more A/Ds into the computer system along with one or more processors and one or more storage media). All of those arrangements, and combinations thereof, fall within the scope of the present disclosure or appended claims.

The computer system 299 is structured, connected, and programmed so as to calculate an estimated transverse position of the one or more primary electric arcs 30 within the arc gap 115. That calculation can be performed in any suitable way using any suitable computational algorithm, modeling, or technique. The calculation of the estimated primary arc position is based at least in part on (i) longitudinal position of the arc gap, and (ii) two or more of the measured magnetic field components along with the corresponding sensor position(s) or calibration parameter(s). In some examples, the calculation is also based at least in part on the magnitude of the input electric current or the primary electric current. In some examples, the longitudinal position of the arc gap 115 is a known input parameter; in some examples, the longitudinal position of the arc gap 115 is estimated based at least in part on one or more operational parameters, e.g., electrode weight, elapsed time of operation of the arc furnace (i.e., melt time), current or magnetic field fluctuations arising from electrode weldments, and so forth; in some examples, the longitudinal position of the arc gap 115 is estimated based at least in part on the magnetic field components measured by the sensors 200. In some examples, measured values of the multiple magnetic field components measured by some or all of the magnetic field sensors 200 are included in a set of equations that also includes the position of the arc gap 115 (known, measured, or estimated) and the calibration parameter(s) or sensor position for each corresponding sensor; the set of equations can also include other known, measured, or estimated operational or structural parameters noted herein (e.g., current magnitude, furnace dimensions, and so forth). In examples wherein measured field values from some, but not all, sensors 200 are employed in a given calculation, the corresponding subset of sensors 200 employed to calculate a given estimated position can vary according to, e.g., the corresponding estimated longitudinal position of the arc gap 115. In some examples, sensor positions, operational parameters (e.g., input current), or structural parameters (e.g., furnace diameter or height, electrode diameter) can appear explicitly in the set of equations; in some examples, one or more such quantities do not appear explicitly, but appear implicitly through their influence on the calibration parameters (e.g., a given sensor can have calibration parameters that vary depending on the size and shape of the furnace, or depending on its position on a given furnace). For purposes of the present disclosure, a calculation is "based at least in part" on a given quantity regardless of whether that quantity influences the calculation explicitly or implicitly. In some examples the set of equations includes only linear equations; in other examples the set of equations can include one or more nonlinear equations. One specific example illustrating how such a calculation can be performed is disclosed in the '059 patent (albeit for a ring of sensors at only a single longitudinal position).

In some examples, the one or more corresponding calibration parameters for each of the sensors 200 are derived from calculations of position-dependent magnetic fields arising from simulated electric currents within a simulated current-containing volume. In some examples, multiple simulations are run; in each run of the simulation a single simulated primary electric arc is placed at a corresponding transverse position within a simulated arc gap at a corresponding longitudinal position within the simulated current-containing volume, and the simulated primary current flows through simulated first and second conductors and the simulated primary arc. In some examples a simulated return current flows in the opposite direction along the lateral periphery of the current-containing volume (e.g., to simulate the return current flowing along the lateral walls of the crucible 101). For each run of the simulation, the resulting magnetic field components are calculated as a function of position at least along the lateral periphery of the simulated current-containing volume (and within its interior as well, if needed or desired), using Maxwell's equations or any suitable subset or approximation thereof (e.g., Ampere's Law or the Biot-Savart Law) and using any suitable computational technique (e.g., the finite element method). Multiple runs of the simulation are performed, with the simulated primary arc located at corresponding different transverse positions, and with the simulated arc gap located at corresponding different longitudinal positions. In one specific example, magnetic field components are calculated for 27 different primary arc positions at each of 30 different longitudinal positions of the arc gap, for a total of 810 runs of the simulation. In examples of a so-called coaxial furnace, in which the input current 20 flows through a vertical conductor into the top of the electrode 110, certain simplifying approximations can be made in the simulations, based on assumed symmetries of the furnace 100. In so-called non-coaxial examples, wherein, e.g., as in FIGS. 2 and 3, the input current 20 flows into the electrode 110 through a transverse conductor 104, a full 3D calculation typically must be performed in the simulations.

With the calculated field values in hand, multiple sensor positions are selected arranged around the lateral periphery of the current-containing volume. The multiple sensor locations are arranged among two or more distinct longitudinal positions and among two or more distinct circumferential positions around the lateral periphery of the current-containing volume. In some examples, the sensor positions are arranged in two or more rings located at corresponding distinct longitudinal positions, with each ring including multiple sensor positions at a single longitudinal position but at corresponding distinct circumferential positions. In the examples of FIGS. 1 through 3, three rings of sensors 200a, 200b, and 200c are employed. In FIG. 1 each of the three rings includes four sensors 200a, 200b, or 200c; in the cross-sections of FIGS. 2 and 3 only two sensors 200a, 200b, or 200c of each ring are visible. Note that the "rings" do not necessarily correspond to an actual mechanical ring structure, but only to the geometric arrangement of multiple sensor positions that make up the ring (i.e., at the single longitudinal position but multiple distinct circumferential positions). Note that "at a single longitudinal position" can denote a subset of the sensors 200 that are at substantially the same longitudinal position, or in some instances can denote a subset of the sensors 200 that fall within a sufficiently narrow range of longitudinal positions to enable their respective measured field components to be used together in certain calculations that depend on longitudinal position (discussed further below). In addition to the multiple rings, additional sensor positions can be located at longitudinal positions that differ from any of the rings, e.g., a longitudinal line of 5 sensors 200d through 200h is employed in addition to three rings 200a through 200c in the examples of FIGS. 1 through 3. Other numbers or arrangements of the non-ring sensors can be employed. More generally, the sensors 200 need not be arranged in any rings or longitudinal lines, provided that sensors 200 are located at multiple distinct longitudinal positions and multiple distinct circumferential positions, and those positions are known accurately. Other examples of suitable arrangements can include, e.g., one or more spirals, or a random scattering of sensors.

The simulations (however they are performed) yield magnetic field components expected to be measured at a given sensor location for a primary electric arc located at any one of the many combinations of transverse arc position and longitudinal arc gap position used in the simulations. From those calculated field components, one or more calibration parameters can be determined for each sensor 200; in many examples, the one or more calibration parameters of a given magnetic sensor 200 will vary with respect to the longitudinal position of the arc gap. The number and type of calibration parameters required to characterize each or the sensors 200 depends on the nature of the mathematical model used in the simulations or to preform subsequent calculations using those parameters. Within the scope of the present disclosure or appended claims, myriad measurement and computation schemes can be devised and implemented for generating suitable calibration parameters for the magnetic sensors 200 and for estimating the position of an electric arc using those parameters in conjunction with measured magnetic field components. Some examples are described below.

In some examples, a set of linear equations can be constructed from the simulation data, in which each simulated current (at a known transverse position and at a known arc gap longitudinal position) is expressed as a linear combination of a subset of calculated magnetic field components, each multiplied by a corresponding yet-to-be-determined calibration parameter. In some examples, all field components calculated at all sensor positions can be included in each equation, In some examples, each equation can include only a corresponding subset of less than all of those calculated field components; the included field components can be selected for each equation on any suitable basis, e.g., proximity of the corresponding sensor position to the simulated arc gap longitudinal position. In some examples, the set of equations can be solved to determine the calibration parameters.

To estimate a location of a real primary electric arc 30 at an unknown position within a real arc furnace 100, those same equations can be used, with the now-determined calibration parameters and a set of magnetic field components measured by the real sensors 200, to calculate a distribution of current magnitudes among the simulated arc positions. That raw distribution can be used as an estimate of the primary arc position, e.g., as a probability density distribution. Alternatively, a centroid of that raw current distribution can be calculated and used as an estimated position of the primary electric arc 30. In some instances, magnetic field components and calibration parameters of all sensors 200 can be used together and used to estimate the primary arc transverse position, and perhaps also the arc gap longitudinal position (if it is not known or estimated by other means). In other instances, only a subset of the sensors are employed together for a given calculation (e.g., for a given estimated longitudinal position of the arc gap, only sensors within a certain longitudinal distance of the arc gap might be employed).

Figure 4:
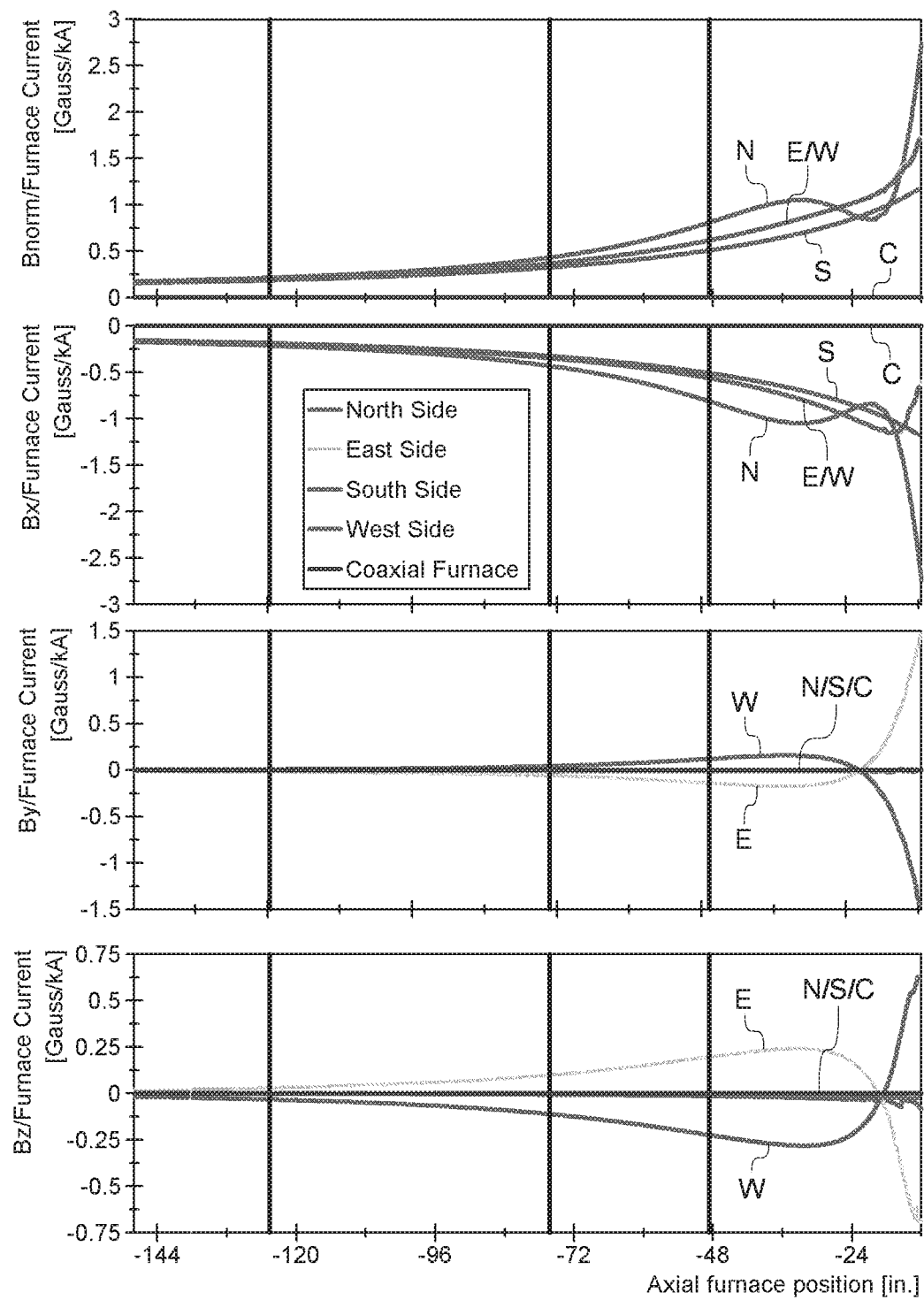
FIG. 4 includes several graphs of dependence on longitudinal position of calculated magnetic field components arising from a simulated electric arc within a simulated non-coaxial arc furnace.

The calibration parameters can be calculated so as to compensate for other magnetic fields that might affect the magnetic field components measured by the sensors 200. For example, an arc furnace 100 typically includes external current pathways that carry the input electric current 20 to the electrode 110 or that carry the return current 24 from the furnace walls (e.g., the transverse conductors 104 and 106 shown in FIGS. 2 and 3, carrying the input and return currents 20 and 24, respectively). Electric currents carried by those elements produce magnetic fields that are detected and measured by the sensors 200, and those additional measured fields can introduce error into the estimation of the transverse position of the primary arc 30 in a non-coaxial furnace. FIG. 4 shows an example of the variation in magnetic field components, as a function of longitudinal position, that can arise in a non-coaxial furnace arrangement. To remove that source of error, the simulations described above can include suitably arranged simulated external current pathways, and the magnetic fields arising therefrom, so that the calibration parameters generated from the simulation data automatically account for those additional fields. Similarly, the simulations can include the earth's magnetic field, so that it also can be accounted for in the calibration parameters calculated from the simulation data. Note that the earth's magnetic field varies by location on the surface of the earth; the simulations are run using the magnetic field value for the intended location of the arc furnace, and the resulting calibration parameters calculated from the simulation data are specific to that furnace location. External magnetic fields arising from other sources (e.g., from one or more adjacent arc furnaces) can be similarly incorporated into simulations and thereby accounted for in the resulting calibration parameters. If an adjacent arc furnace is similarly equipped with magnetic sensors, field components measured by those sensors can be included in the calculated estimate of the primary arc transverse position. If an adjacent arc furnace is sufficiently far away, its current can be approximated as a simple line current and the resulting magnetic field components included in the calculation, e.g., as a substantially uniform offset.

Calculation of sensor calibration parameters based on simulation data typically assumes that the sensors 200 are perfectly aligned (e.g., the three orthogonal measurement axes of a 3D sensor are perfectly aligned along the longitudinal and transverse axes of the arc furnace). However, this is typically not the case in a real system of sensors 200 positioned around an arc furnace 100; there is often some small deviation of the orientation of each sensor 200 from its idealized orientation used in the simulation. Those deviations can be the same for multiple sensors (e.g., a framework or bracket holding multiple sensors 200 is misaligned relative to the arc furnace 100) or can vary, often somewhat randomly, among the sensors (e.g., random misalignment of individual sensors 200 relative to the arc furnace 100); both of those types of misalignment can occur simultaneously. In some examples, directional corrections can be incorporated into the calculation of calibration parameters. In some instances, those directional corrections can be based on magnetic field components arising from a real test current (not simulated) and measured by the sensors. In one arrangement, a straight conducting rod is placed within an arrangement of the sensors 200 (e.g., with the sensors 200 mounted on a jig, bracket, framework, or other hardware that will be used for subsequent attachment of the sensors to the arc furnace 100, or with the sensors mounted on the arc furnace 100 and with the conducting rods positioned within the arc furnace 100), and a test current is run through the rod. Magnetic field components measured by the mounted sensors 200 are compared to magnetic field components calculated in a simulation of the test current flowing through the rod among the sensors 200, and that comparison is used to correct the calibration parameters of the sensors 200.

As noted above, in some examples the multiple sensor positions include two or more rings of sensor positions, wherein each ring includes multiple sensor positions arranged at substantially the same longitudinal position along the current-containing volume and at multiple distinct circumferential positions around the lateral periphery of the current-containing volume. In some of those examples, the multiple sensor positions include three or more of the rings of sensor positions (e.g., sensor rings 200a, 200b, and 200c shown in FIGS. 1-3). In some examples that include rings of sensor positions, the sensors 200 at the positions in the rings can be arranged so as to measure magnetic field components in at least both substantially transverse dimensions. Such an arrangement can be advantageously employed in some examples for estimating the primary arc transverse position, particularly when the arc gap 115 is relatively near the longitudinal position of one of the rings, e.g., in furnaces of typical sizes, within about two feet of a sensor ring 200a/200b/200c in a non-coaxial furnace, or within about 8 feet of a sensor ring in a coaxial furnace (in each case, with suitable longitudinal variation of the calibration parameters according to the estimated longitudinal position of the arc gap 115). In some examples that include two or more rings of sensor positions, two or more corresponding preliminary estimates of the transverse position of the primary arc can be calculated, with each of those preliminary estimates being calculated using magnetic field components measured by sensors 200 of only one of the rings (or possibly including additional sensors 200 that are within a limited longitudinal distance of that ring). The estimated position of the primary arc 30 can then be calculated as a weighted average of the two or more preliminary estimates. Each preliminary estimate can be weighted according to its longitudinal distance from the arc gap longitudinal position, with the weight factor of a given ring decreasing with increasing longitudinal distance between that ring and the arc gap position. A linear variation of the weight factor with longitudinal distance can be employed, or any other suitable or desirable longitudinal variation of the weight factors can be employed.

In one specific example method using the example arrangements of FIGS. 1-3, a first preliminary estimated transverse position of the arc 30 can be calculated using field values measured by only the sensor ring 200a, a second preliminary estimated position calculated using only the sensor ring 200b, and a third preliminary estimated position calculated using only the sensor ring 200c. For arc gap positions below the ring 200a, only the first preliminary estimated position (calculated based on the sensor ring 200a) is employed as the estimated arc position; for arc gap positions above the ring 200c, only the third preliminary estimated position (calculated based on the sensor ring 200c) is employed as the estimated arc position. For arc gap positions between the rings 200a and 200b, a suitably weighted average of the first and second preliminary estimated arc positions (calculated using the sensor rings 200a and 200b, respectively) are employed to calculate the estimated arc position; for arc gap positions between the rings 200b and 200c, a suitably weighted average of the second and third preliminary transverse arc positions (calculated using the sensor rings 200b and 200c, respectively) are employed to calculate the estimated arc position.

In an electric arc furnace, it is desirable for the entire input current 20 to flow through the conductors 110 and 120, and as the primary arc 30 across the arc gap 115, as the primary current 22 (e.g., as in FIG. 2); in such instances the input current 20 and the primary current 22 are substantially equal. In some other instances however, one or more secondary arcs 32 can appear, typically only transiently, that carry a secondary current 26, typically between the electrode 110 and the side wall of the crucible 101 (e.g., as shown in FIG. 3; such a secondary arc 32 is often referred to as a side arc). In such instances the input current 20 is substantially equal to a sum of the primary and secondary currents 22 and 26. Side arcing typically is regarded as undesirable in an arc furnace. First, it diverts a portion of the input current 20 away from the primary arc 30 as the secondary current 26, reducing the amount of electrical energy delivered to the end of the electrode 110 to drive the remelting process. Second, the side arc 32 can result in a distorted shape of the lower end or side surface of the electrode 110, which can interfere with subsequent remelting. Third, a large flow of secondary current 26 to the furnace wall via the side arc 32 results in localized heating of a relatively small area of the crucible wall, which can introduce crucible material (often copper) as an impurity into the ingot 120, or can create a safety hazard by creating a "hot spot" on the crucible wall, perhaps even leading to failure of the crucible wall. It would be desirable to provide a way to detect, and perhaps also measure or localize, secondary arcing when it occurs.

To achieve that purpose, in some examples two or more of the multiple sensors 200 are arranged so as to measure a magnetic field component in a substantially longitudinal dimension (sometimes referred to as a "z-field" component), in addition to the two transverse magnetic field components. The computer system 299 is structured, connected, and programmed so as to so as to recognize one or more sets of measured magnetic field components that are indicative of a secondary electric current 26 flowing in a predominantly transverse direction as a secondary electric arc 32 between the first or second electrode and the chamber. The calculation is based at least in part on the longitudinal position of the arc gap 115, and two or more of the measured magnetic field components along with the corresponding sensor position(s) or calibration parameter(s).

Figure 5A:
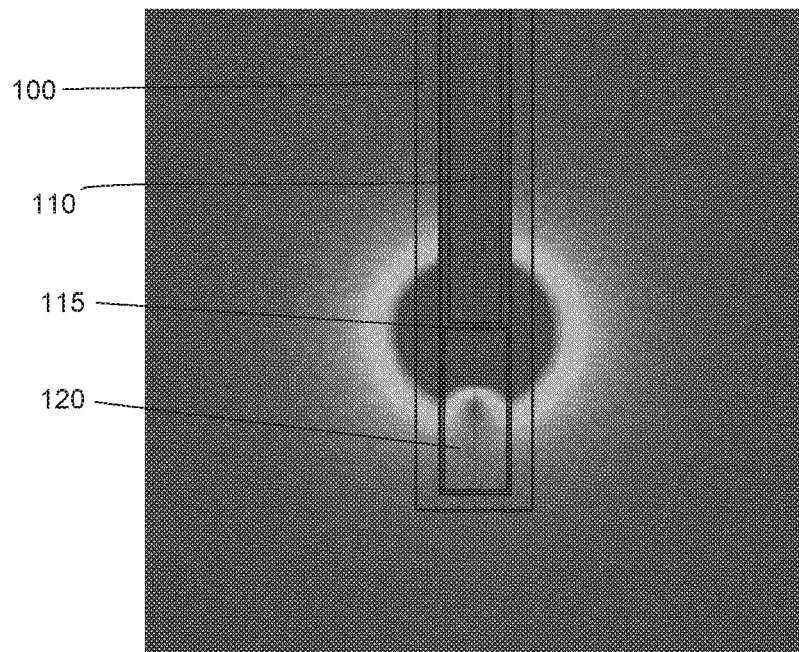
FIGS. 5A and 5B are schematic contour plots of the magnetic field magnitude in an arc furnace with a longitudinal primary arc (FIG. 5A) and a transverse secondary arc (FIG. 5B).
Figure 5B:
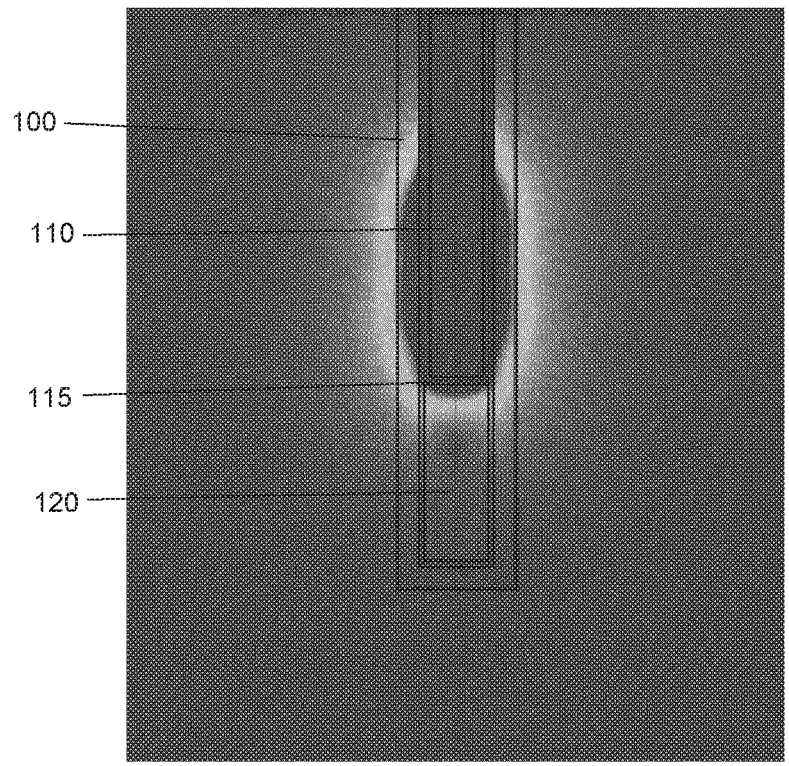
Figure 6A:
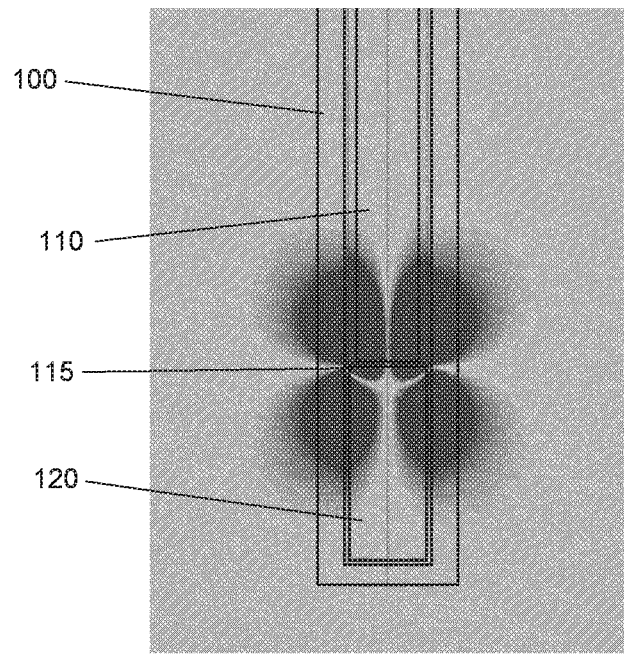
FIGS. 6A and 6B are schematic contour plots of the magnetic field longitudinal component in an arc furnace with a longitudinal primary arc (FIG. 6A) and a transverse secondary arc (FIG. 6B).
Figure 6B:
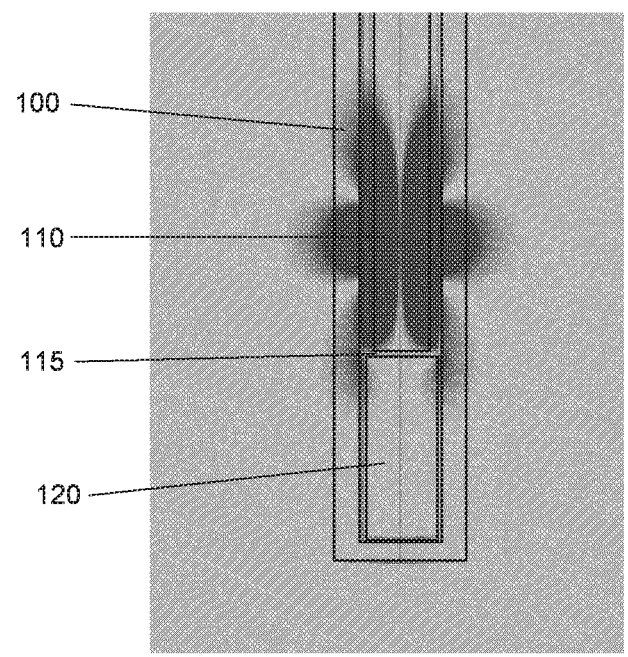

In many instances, a primary arc 30 produces a spatial distribution of magnetic field magnitude or magnetic field longitudinal component (e.g., as in FIGS. 5A and 6A, respectively) that differs qualitatively from analogous spatial distributions of magnitude or longitudinal component arising from a side arc 32 (e.g., as in FIGS. 5B and 6B, respectively). In some examples, in the absence of a secondary arc 32, the magnitude or longitudinal component of the magnetic field is nearly symmetric in the longitudinal direction, centered about the arc gap 115. In other words, in the absence of a secondary arc 32, the magnitude or longitudinal component of the magnetic field at a certain distance above the arc gap 115 is substantially equal to the magnitude or longitudinal component at that same distance below the arc gap 115 and at the same circumferential position. In such examples, if a secondary arc 32 is present, however, that longitudinal symmetry is distorted and the magnitudes of those two measured magnitudes or longitudinal field components can differ. That longitudinal asymmetry of the magnitude or longitudinal field components (about the arc gap 115) is a recognizable signature of the presence of a secondary arc 32 between, e.g., the electrode 110 and the side wall of the crucible 101. A suitable threshold value can be selected for that asymmetry as the criterion for estimating that a secondary arc 32 is present. Such a threshold can be an absolute value, or can be suitably normalized or offset, e.g., with respect to a baseline established by field values previously measured during operation of the arc furnace 100. Longitudinal variation of one or more other measured field components (e.g., transverse field components) can be employed if suitable or desirable.

In other examples, azimuthal variation (at a given longitudinal position) of the magnitude or one or more components of the magnetic field can be analyzed to enable recognition of the presence of a side arc 32. In some examples, azimuthal variation of magnetic field magnitude, or specific components thereof, arising from a primary arc 30 typically includes an approximately sinusoidal variation with a single maximum and a single minimum about the periphery of the current-containing volume 10. Azimuthal variation, of magnetic field magnitude or components, arising from a side arc 32 typically differs from that relatively simple quasi-sinusoidal variation. Observed deviation from the simple variation can be an indication of the presence of a side arc 32.

A variety of actions can be taken based on a determination that a side arc 32 is present, e.g., simply noting the occurrence of the secondary arc 32 in documentation associated with that particular ingot 120, altering the input current 20 so as to suppress the secondary arc, cutting off the input current 20 to shut down the remelting process entirely as a safety measure, or other suitable, desirable, or necessary action.

In some examples, the computer system 299 can be further structured, connected, and programmed so as to calculate an estimated magnitude of the secondary electric current or an estimated position of the secondary electric arc. Simulations, similar to those described above for the primary electric arc 30, typically would be needed in order to provide the necessary calibration parameters for such an estimation of secondary arc position or secondary current magnitude. Such a calculation can be based at least in part on the magnitude of the input current, the longitudinal position of the arc gap, and two or more of the measured magnetic field magnitude or components along with the corresponding sensor position(s) or calibration parameter(s), and in some examples can be carried out in a manner similar to any of the examples described above.

As already noted, as the remelting process proceeds, the ingot 120 grows, the electrode 110 shrinks, and the arc gap 115 moves upward through the arc furnace 100. The water jacket 103 around the crucible 101 is employed to control the solidification rate and conditions to yield the desired properties of the ingot material. The electrode 110 has a smaller diameter than the crucible 101 (and hence the ingot 120 that is formed) to avoid current flow from the electrode 110 to the walls of the crucible 101; consequently, the electrode 110 must be moved downward at the correct rate during operation of the furnace in order to maintain the correct height of the arc gap 115 (i.e., the distance between the electrode 110 and the ingot 120) as the electrode 110 melts away and the ingot 120 grows. In some typical examples of an arc furnace, the inner diameter of the crucible 101 is about 6 inches to about 40 inches, which is also the approximate diameter of the ingot 120 that is formed. As the ingot solidifies it contracts and pulls away from the furnace side walls leaving a small gap (e.g., ca. 0.05 inches to 0.3 inches). As the remelting process proceeds, at relatively short portion (e.g., ca. 2 inches to 12 inches or more) at the top of the ingot 120 remains in contact with the furnace side walls, and provides a path for return current 24. In some examples, a portion of the return current 24 can flow through the bottom of the ingot 120 into the walls of the crucible 101.

Figure 7A:
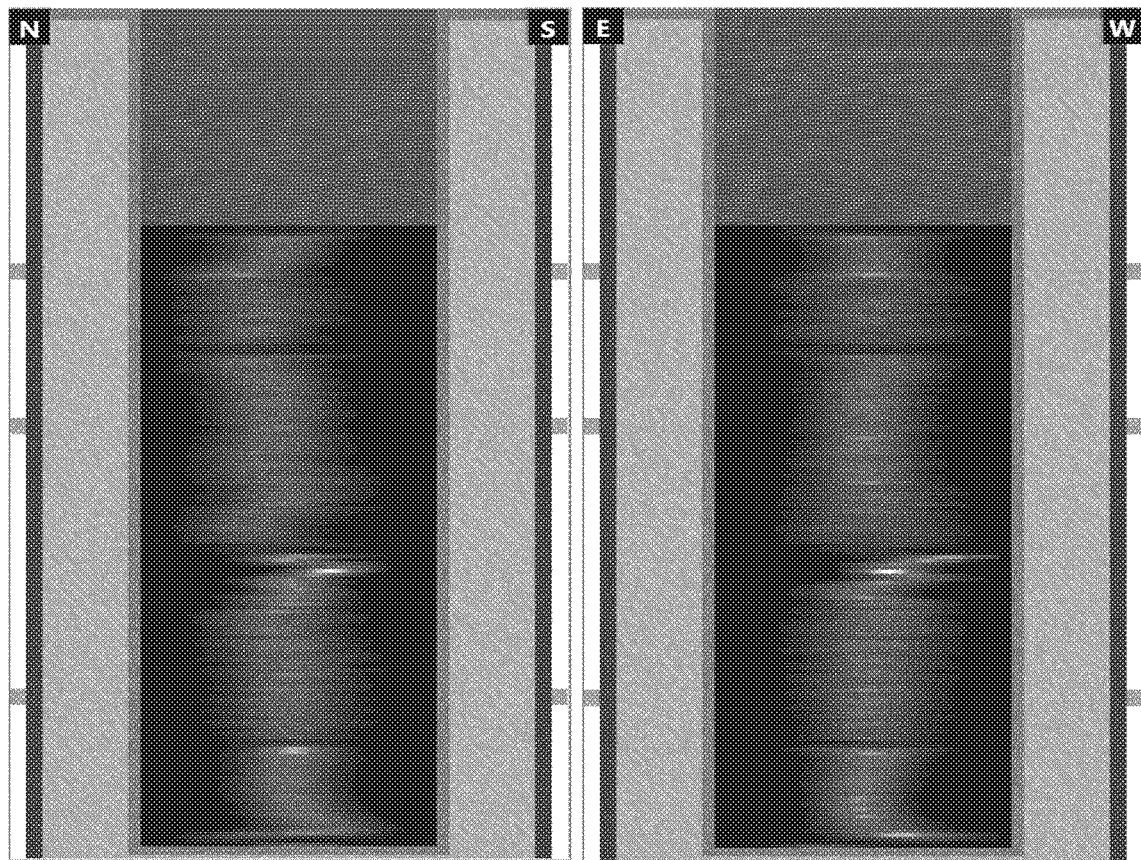
FIG. 7A shows an example of a measured distribution of estimated transverse arc positions along the length of an ingot.
Figure 7B:
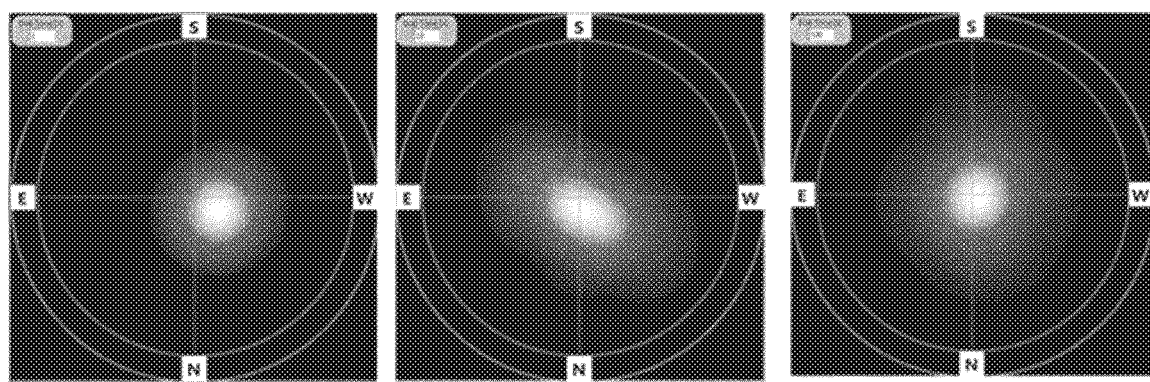
FIG. 7B show examples of measured distributions of transverse arc position across an ingot averaged over 1 second, 10 seconds, and 100 seconds, respectively.

The longitudinal position of the arc gap 115 (equivalently, the height of the ingot 120) changes monotonically as the remelting process proceeds (in the arc furnace example), and so is a monotonic function of the melt time (i.e., the elapsed time beginning with the initiation of the flow of the input current 20; the entire range of melt times beginning with initiation of the input current flow and ending with termination of the input current flow is referred to herein as the melt period). It is important to have a sufficiently accurate estimate of the arc gap longitudinal position as a function of melt time so that the estimated transverse arc position (also a function of melt time) can be correlated with the corresponding longitudinal arc gap position, and in turn correlated with any observed variation of material properties of the ingot 120 along its longitudinal dimension. In some examples, the arc gap longitudinal position is also an input for the calculation of the estimated transverse position of the primary arc 30. The computer system 299 is structured, connected, and programmed in any suitable way so as to calculate an estimated arc gap longitudinal position that changes with melt time as the input current 20 flows. In some examples, the arc gap longitudinal position is assumed to be a linear function of melt time, with the slope determined by melt rate (mass/time), furnace inner diameter, and material density, and can be calculated on that basis or directly measured (e.g., if the rate of decrease of the weight of the electrode 110 is available as a function of melt time, such as in an arc furnace equipped with a load cell or other device for monitoring the changing weight of the electrode 110). An estimated arc gap longitudinal position is calculated based on the particular melt time and the slope, and that value is correlated with the corresponding estimated transverse position of the arc calculated at that particular melt time. In some examples, as described above, the arc gap estimated longitudinal position is used in the calculation of the arc estimated transverse position; in other examples, the arc transverse position can be estimated without using the arc gap position in the calculation. The term "correlated" means that the arc gap longitudinal position (or equivalently, the position along the length of the ingot 120) at a given melt time is associated with the arc transverse position estimated at that given melt time (whether or not the arc gap longitudinal position was used in the calculation of the arc transverse position). A dataset that includes estimated transverse positions of the arc 30 (perhaps averaged over a suitable time interval) over the entire length of the ingot 120 (equivalently, over the entire melt time), or a portion thereof, can be generated and stored, and employed for quality or process control, or characterization of or documentation for the ingot 120. In the example of FIG. 7A, a distribution of transverse arc position (in two orthogonal transverse dimensions in the two panels) is plotted along the length of an ingot; a significant transverse deviation of the arc position can be seen about halfway along the length of the ingot. In the example of FIG. 7B, a distribution of transverse arc position is plotted along the two transverse dimensions averaged over 1 second (left panel), 10 seconds (middle panel), and 100 seconds (right panel).

Figure 8C:
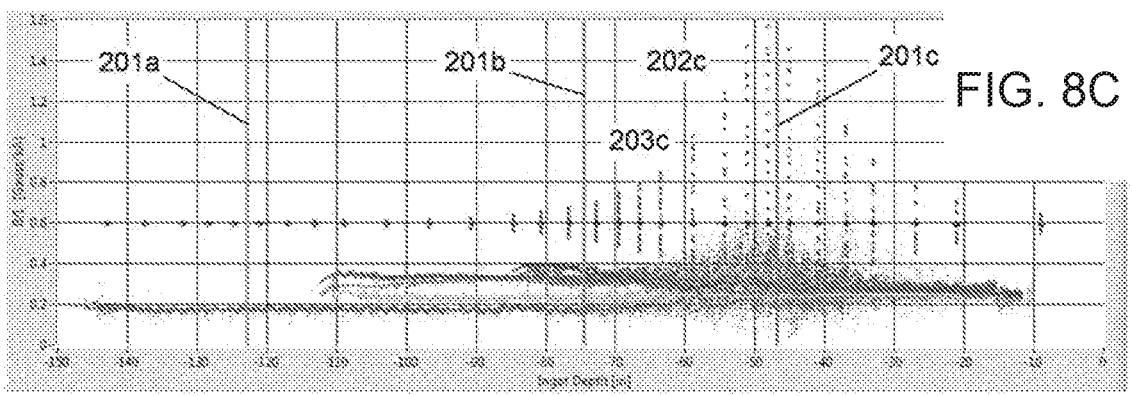
FIGS. 8A, 8B, and 8C are schematic plots of measured and calculated magnetic field components as a function of arc gap longitudinal position for three different sensor rings.
Figure 8B:
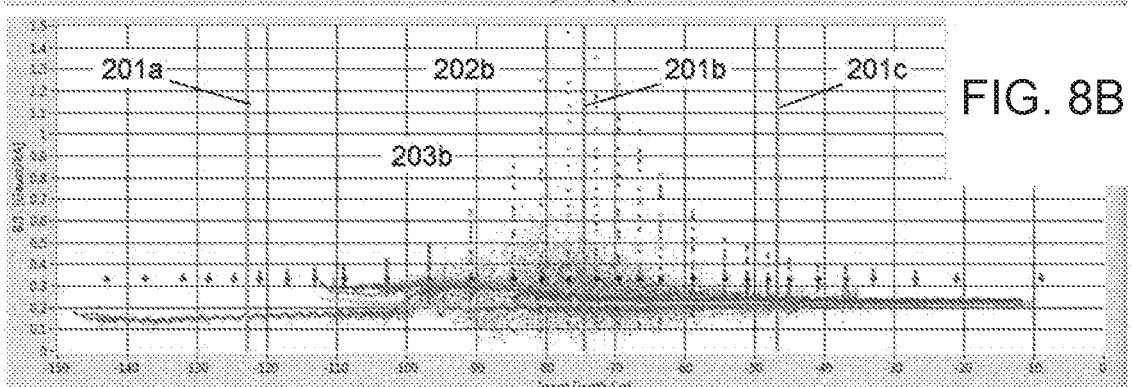
Figure 8A:
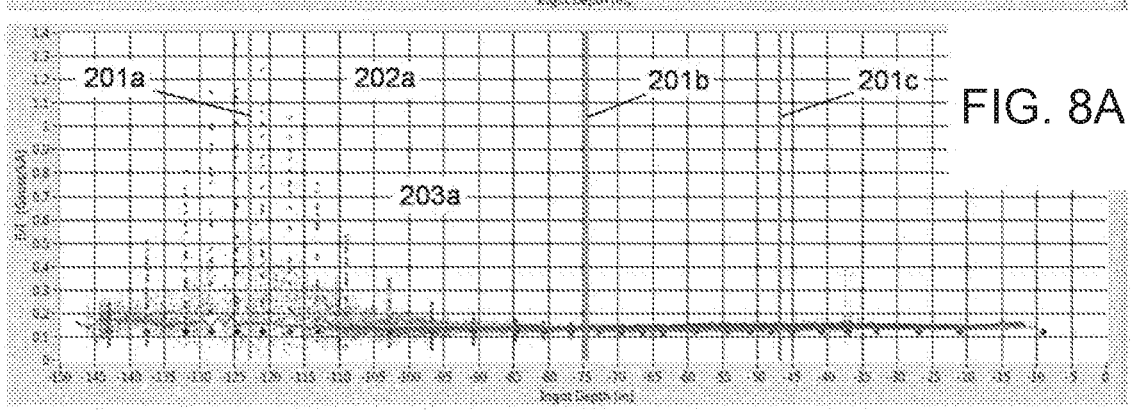

In some examples, the magnetic field components measured by some or all of the sensors 200 can be employed to estimate the longitudinal position of the arc gap 30 during the remelting process. For example, it has been observed in some examples (e.g., as in FIGS. 8A, 8B, and 8C) that the average magnetic field magnitude measured by a subset of the sensors 200 at the same or nearby longitudinal positions (e.g., the sensors of one ring) goes through a maximum with respect to the melt time as the arc gap 115 passes the longitudinal position of that subset of sensors 200. The respective longitudinal positions 201*a*/201*b*/201*c* of the three rings of sensors 200*a*/200*b*/200*c* are shown in the example of FIGS. 8A, 8B, and 8C, along with calculated (202*a*/202*b*/202*c*) and measured (203*a*/203*b*/203*c*) field values of the respective sensors 200*a* (FIG. 8A), 200*b* (FIG. 8B), and 200*c* (FIG. 8C). It has also been observed in some examples (e.g., as in FIGS. 9A and 9B) that the average longitudinal component of the magnetic field measured by such a subset of sensors 200 goes through a minimum with respect to melt time as the arc gap 115 passes the longitudinal position of the that sensor subset. Each such longitudinal subset of the sensors 200 can therefore act as a calibration point for estimating the arc gap longitudinal position during remelting process. As the remelting process progresses, the computer system 299 recognizes when the average magnetic field magnitude for a particular longitudinal sensor subset goes through a maximum (either by reaching a predetermined value, or by reaching a relative maximum value with respect to melt time and then beginning to decrease), or when the average longitudinal magnetic field component goes through a minimum. The longitudinal position that characterizes that longitudinal subset is used to estimate the longitudinal position of the arc gap 115 at the melt time when that maximum occurred. In some examples, the longitudinal subset position is the estimated arc gap position; in other examples, the longitudinal sensor subset position is corrected by a suitable predetermined longitudinal offset, e.g., if it is observed during a calibration procedure or simulation that the maximum or minimum measured field magnitude or component occurs, not at the sensor subset position, but at some consistent longitudinal offset before or after (e.g., in the examples of FIGS. 9A and 9B, the minimum measured field component occurs slightly before the arc gap 115 reaches the longitudinal positions of the sensors rings 200*a*/200*b*/200*c*). The arc gap longitudinal position can be estimated for one or more such longitudinal subsets of the sensors 200, and the estimated positions and corresponding melt times can serve as fixed calibration points in the dependence of the arc gap longitudinal position with melt time. Intermediate arc gap positions can be interpolated between such fixed calibration points, or between a fixed calibration point and a beginning or end point of the remelting process.

In other examples, the electrode 100 can provide one or more fixed calibration points in the arc gap position versus melt time curve. In some instances, an aggregated electrode 100 is fabricated by assembling and welding together multiple pieces of the material to be remelted, and the resulting weldments in the electrode 110 are at known positions along the electrode 110. It has been observed during remelting processes that, upon the arc gap 115 reaching and passing such a weldment, a recognizable variation in the current, voltage, or one or more measured magnetic field components is often observed. If so, then the melt time at which such a variation is recognized corresponds to the melt time when the arc gap passes the known weldment position, thereby establishing a fixed calibration point. In a manner similar to that described above, one or more such fixed calibration points can be employed to interpolate the entire arc-gap-longitudinal-position-versus-melt-time curve.

Portions of the systems and methods disclosed herein can be implemented as or with general or special purpose computers or servers or other programmable hardware devices programmed through software, or as hardware or equipment "programmed" through hard wiring, or a combination of the two. A "computer" or "server" can comprise a single machine or can comprise multiple interacting machines (located at a single location or at multiple remote locations). Computer programs or other software code, if used, can be implemented in tangible, non-transient, temporary or permanent storage or replaceable media, such as by including programming in microcode, machine code, network-based or web-based or distributed software modules that operate together, RAM, ROM, CD-ROM, CD-ft CD-R/W, DVD-ROM, DVD±R, DVD±R/W, hard drives, thumb drives, flash memory, optical media, magnetic media, semiconductor media, or any future computer-readable storage media. Electronic indicia of any measured or calculated quantities, any calibration or modeling parameters, any programming code or instructions, and so forth can be read from, received from, written to, or stored on any of the tangible, non-transitory computer-readable media mentioned herein.

In addition to the preceding, the following examples fall within the scope of the present disclosure or appended claims:

Example 1. An apparatus for estimating a location of an electric arc, the apparatus comprising a set of multiple magnetic field sensors, a data acquisition system operatively coupled to the magnetic field sensors, and a computer system operatively coupled to the data acquisition system, wherein: (a) the multiple magnetic field sensors are arranged around a lateral periphery of a current-containing volume into which an input electric current flows and within which at least a portion of the input current flows, in a predominantly longitudinal direction as a primary electric current, (i) through at least portions of first and second longitudinal electrical conductors positioned end-to-end within the current-containing volume and separated by an arc gap, and (ii) as one or more primary electric arcs spanning the arc gap and movable in two transverse dimensions within the arc gap between the first and second conductors; (b) each sensor of the set is positioned at a corresponding one of multiple distinct sensor positions, and the sensor positions are arranged among two or more distinct longitudinal positions along the current-containing volume and among two or more distinct circumferential positions around the lateral periphery of the current-containing volume; (c) each sensor of the set is arranged so as to measure magnetic field components in two or more spatial dimensions and is characterized by one or more corresponding calibration parameters; (d) the data acquisition system is structured and connected so as to convey to the computer system signals from the multiple sensors indicative of the corresponding measured magnetic field components; and (e) the computer system comprises one or more electronic processors and one or more digital storage media coupled thereto, and is structured, connected, and programmed so as to calculate an estimated transverse position of the one or more primary electric arcs within the arc gap, that calculation being based at least in part on longitudinal position of the arc gap, and two or more of the measured magnetic field components along with one or more corresponding sensor positions or calibration parameters.

Example 2. The apparatus of Example 1 wherein each sensor of the set is arranged so as to measure magnetic field components in three spatial dimensions.

Example 3. The apparatus of any one of Examples 1 or 2 wherein the calculation is based at least in part on magnitude of the input electric current or the primary electric current.

Example 4. The apparatus of any one of Examples 1 through 3 wherein the one or more corresponding calibration parameters for each sensor are derived from calculations, at multiple distinct transverse positions and at multiple distinct longitudinal positions of a simulated arc gap, of magnetic field components at the corresponding sensor position arising from a simulated input current flowing in a single simulated primary electrical arc, so that for one or more of the multiple sensors the corresponding one or more calibration parameters vary with the longitudinal positon of the arc gap.

Example 5. The apparatus of any one of Examples 1 through 4 wherein one or more calculations include corrections for magnetic field components arising from external conductors carrying the primary current into the current-containing volume or carrying a return current out of the current-containing volume.

Example 6. The apparatus of any one of Examples 1 through 5 wherein one or more calculations include measured directional corrections to the orientations of the measured magnetic field components for each sensor.

Example 7. The apparatus of any one of Examples 1 through 6 wherein one or more calculations include measured corrections arising from external magnetic fields in which the current-carrying volume is immersed.

Example 8. The apparatus of any one of Examples 1 through 7 wherein the multiple sensor positions include two or more rings of sensor positions, wherein each ring includes multiple sensor positions arranged at substantially the same longitudinal position along the current-containing volume and at multiple distinct circumferential positions around the lateral periphery of the current-containing volume.

Example 9. The apparatus of Example 8 wherein the multiple sensor positions include three or more of the rings of sensor positions.

Example 10. The apparatus of any one of Examples 8 or 9 wherein those sensors positioned at corresponding sensor positions of the two or more rings are arranged so as to measure magnetic field components in two substantially transverse dimensions.

Example 11. The apparatus of any one of Examples 8 through 10 wherein the multiple sensor positions include one or more sensor positions that are positioned at corresponding longitudinal positions along the current-containing volume that differ from the corresponding longitudinal positions of the two or more rings of sensor positions.

Example 12. The apparatus of any one of Examples 8 through 11 wherein the estimated transverse position of the one or more primary electric arcs is a weighted average of estimated arc transverse positions calculated for each ring using measured field components from sensors at corresponding sensor positions of only that ring, and the estimated arc transverse positions for each ring are weighted according to a corresponding longitudinal distance between that ring and the estimated longitudinal position of the arc gap, with a corresponding weight factor decreasing with increasing distance between the corresponding ring and the estimated arc gap position.

Example 13. The apparatus of any one of Examples 1 through 12 wherein the current-containing volume is enclosed within a chamber that defines the lateral periphery of the current-containing volume, and the multiple sensor positions are located outside the chamber.

Example 14. The apparatus of Example 13 wherein two or more of the multiple sensors are arranged so as to measure a magnetic field component in a substantially longitudinal dimension, and the computer system is structured, connected, and programmed so as to recognize one or more sets of measured magnetic field magnitudes or longitudinal components that are indicative of a secondary electric current flowing in a predominantly transverse direction as a secondary electric arc between the first or second conductor and the chamber, that recognition being based at least in part on the magnitude of the input current, an estimated longitudinal position of the arc gap, and two or more of the measured longitudinal magnetic field components along with one or more corresponding sensor positions or calibration parameters.

Example 15. The apparatus of Example 14 wherein the computer system is structured, connected, and programmed so as to calculate an estimated magnitude of the secondary electric current or an estimated position of the secondary electric arc, that calculation being based at least in part on the magnitude of the input current, an estimated longitudinal position of the arc gap, and two or more of the measured longitudinal magnetic field components along with one or more corresponding sensor positions or calibration parameters.

Example 16. The apparatus of any one of Examples 14 or 15 wherein, with no secondary current flowing, the input current is substantially equal to the primary current.

Example 17. The apparatus of any one of Examples 14 or 15 wherein, with one or more secondary electric arcs present, the input current is substantially equal to a sum of the primary and secondary currents.

Example 18. The apparatus of any one of Examples 13 through 17 further comprising the chamber, wherein the chamber comprises an electric arc furnace, the first conductor comprises an electrode of the furnace, the second conductor comprises an ingot formed within the furnace, and the furnace is arranged so that the arc gap moves longitudinally through the furnace as the input current flows during a melt period, causing the electrode to melt and shrink and the ingot to grow.

Example 19. The apparatus of Example 18 wherein the computer system is structured, connected, and programmed so as to calculate an estimated arc gap longitudinal position that changes with melt time as the input current flows during the melt period.

Example 20. The apparatus of Example 19 wherein the longitudinal position of one or more selected sensors that register a maximum measured magnetic field magnitude, with respect to melt time as the input current flows during the melt period, is used to estimate longitudinal position of the arc gap at the melt time when the selected sensors register that maximum measured magnetic field magnitude.

Example 21. The apparatus of any one of Examples 19 or 20 wherein the longitudinal position of one or more selected sensors that register a minimum measured magnetic field longitudinal component, with respect to melt time as the input current flows during the melt period, is used to estimate longitudinal position of the arc gap at the melt time when the selected sensors register that minimum measured magnetic field longitudinal component.

Example 22. The apparatus of any one of Examples 20 or 21 wherein the selected sensors are arranged in a ring around the periphery of the current-carrying volume at a common longitudinal position.

Example 23. The apparatus of any one of Examples 19 through 22 wherein (i) the electrode includes one or more weldments at known longitudinal positions that produce a recognizable alteration of one or more magnetic field components as the electrode melts and the arc gap passes each weldment, (ii) the computer system is structured, connected, and programmed so as to recognize the alteration detected by one or more of the sensors, and (iii) a longitudinal position of corresponding weldment of the electrode is used to estimate the longitudinal position of the arc gap at a melt time when the alteration occurs.

Example 24. The apparatus of any one of Examples 19 through 23 wherein the computer system is structured, connected, and programmed so as to calculate an estimated arc gap longitudinal position as a function of time as an interpolation between arc gap positions estimated by weldment position, by minimum longitudinal field component detection, or by maximum field magnitude detection.

Example 25. The apparatus of any one of Examples 19 through 24 wherein the arc gap longitudinal position is estimated based at least in part on size, shape, density, and weight of the first longitudinal electrical conductor, and duration and magnitude of the primary current flow.

Example 26. A method, using the apparatus of any one of Examples 1 through 25, for estimating transverse position of one or more primary electric arcs as a function of longitudinal position of an arc gap within an electric arc furnace, during a melt period during which an input electric current flows into the arc furnace and at least a portion of the input current flows, in a predominantly longitudinal direction as a primary electric current, (i) through at least portions of first and second longitudinal electrical conductors positioned end-to-end within the arc furnace and separated by the arc gap, and (ii) as the one or more primary electric arcs spanning the arc gap and movable in two transverse dimensions within the arc gap between the first and second conductors, the method comprising: (A) during the melt period, measuring magnetic field components in two or more spatial dimensions using a set of multiple magnetic field sensors, with each sensor positioned at a corresponding one of multiple sensor positions arranged around a lateral periphery of the arc furnace, wherein the multiple sensor positions are arranged among two or more distinct longitudinal positions along the arc furnace and among two or more distinct circumferential positions around the lateral periphery of the arc furnace, and wherein each sensor is characterized by one or more corresponding calibration parameters; (B) using a data acquisition system structured and connected therefor, conveying from the multiple sensors to a computer system signals from the multiple sensors indicative of the corresponding measured magnetic field components; and (C) using the computer system that is structured, connected, and programmed therefor, for each one of multiple melt times within the melt period, calculating a corresponding estimated transverse position of the one or more primary electric arcs within the arc gap, that calculation being based at least in part on the longitudinal position of the arc gap at the corresponding melt time, and two or more of the magnetic field components, measured at the corresponding melt time, along with one or more corresponding sensor positions or calibration parameters.

It is intended that equivalents of the disclosed example embodiments and methods shall fall within the scope of the present disclosure or appended claims. It is intended that the disclosed example embodiments and methods, and equivalents thereof, may be modified while remaining within the scope of the present disclosure or appended claims.

In the foregoing Detailed Description, various features may be grouped together in several example embodiments for the purpose of streamlining the disclosure. This method of disclosure is not to be interpreted as reflecting an intention that any claimed embodiment requires more features than are expressly recited in the corresponding claim. Rather, as the appended claims reflect, inventive subject matter may lie in less than all features of a single disclosed example embodiment. Thus, the appended claims are hereby incorporated into the Detailed Description, with each claim standing on its own as a separate disclosed embodiment. However, the present disclosure shall also be construed as implicitly disclosing any embodiment having any suitable set of one or more disclosed or claimed features (i.e., a set of features that are neither incompatible nor mutually exclusive) that appear in the present disclosure or the appended claims, including those sets that may not be explicitly disclosed herein. In addition, for purposes of disclosure, each of the appended dependent claims shall be construed as if written in multiple dependent form and dependent upon all preceding claims with which it is not inconsistent. It should be further noted that the scope of the appended claims does not necessarily encompass the whole of the subject matter disclosed herein.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open ended terminology, with the same meaning as if the phrase "at least" were appended after each instance thereof, unless explicitly stated otherwise. For purposes of the present disclosure or appended claims, when terms are employed such as "about equal to," "substantially equal to," "ca.", "greater than about," "less than about," and so forth, in relation to a numerical quantity, standard conventions pertaining to measurement precision and significant digits shall apply, unless a differing interpretation is explicitly set forth. For null quantities described by phrases such as "substantially prevented," "substantially absent," "substantially eliminated," "about equal to zero," "negligible," and so forth, each such phrase shall denote the case wherein the quantity in question has been reduced or diminished to such an extent that, for practical purposes in the context of the intended operation or use of the disclosed or claimed apparatus or method, the overall behavior or performance of the apparatus or method does not differ from that which would have occurred had the null quantity in fact been completely removed, exactly equal to zero, or otherwise exactly nulled.

In the appended claims, any labelling of elements, steps, limitations, or other portions of a claim (e.g., first, second, etc., (a), (b), (c), etc., or (i), (ii), (iii), etc.) is only for purposes of clarity, and shall not be construed as implying any sort of ordering or precedence of the claim portions so labelled. If any such ordering or precedence is intended, it will be explicitly recited in the claim or, in some instances, it will be implicit or inherent based on the specific content of the claim. In the appended claims, if the provisions of 35 USC § 112(f) are desired to be invoked in an apparatus claim, then the word "means" will appear in that apparatus claim. If those provisions are desired to be invoked in a method claim, the words "a step for" will appear in that method claim. Conversely, if the words "means" or "a step for" do not appear in a claim, then the provisions of 35 USC § 112(f) are not intended to be invoked for that claim.

If any one or more disclosures are incorporated herein by reference and such incorporated disclosures conflict in part or whole with, or differ in scope from, the present disclosure, then to the extent of conflict, broader disclosure, or broader definition of terms, the present disclosure controls. If such incorporated disclosures conflict in part or whole with one another, then to the extent of conflict, the later-dated disclosure controls.

The Abstract is provided as required as an aid to those searching for specific subject matter within the patent literature. However, the Abstract is not intended to imply that any elements, features, or limitations recited therein are necessarily encompassed by any particular claim. The scope of subject matter encompassed by each claim shall be determined by the recitation of only that claim.

What is claimed is:

1. An apparatus for estimating a location of an electric arc within an electric arc furnace, the apparatus comprising:
   (a) a chamber of the arc furnace that is structurally arranged so as to enclose a current-containing volume, define a lateral periphery of the current-containing volume, and enclose first and second longitudinal electrical conductors positioned end-to-end within the chamber separated by an arc gap, the chamber being connected so as to enable an input electric current to flow into the current-containing volume, and at least a portion of the input current to flow in a predominantly longitudinal direction as a primary electric current (i) through at least portions of the first and second longitudinal electrical conductors and (ii) as one or more primary electric arcs that span the arc gap and that are movable in two transverse dimensions within the arc gap between the first and second conductors;
   (b) a set of multiple magnetic field sensors that are arranged around the lateral periphery of the current-containing volume with each sensor of the set positioned at a corresponding one of multiple distinct sensor positions, wherein the multiple sensor positions are located outside the chamber and arranged among two or more distinct longitudinal positions along the current-containing volume and among two or more distinct circumferential positions around the lateral periphery of the current-containing volume, and wherein each sensor of the set is arranged so as to measure magnetic field components in two or more spatial dimensions and is characterized by one or more corresponding calibration parameters;

(c) a data acquisition system that is structured and connected so as to acquire signals from the multiple sensors indicative of the corresponding measured magnetic field components; and (d) a computer system that comprises one or more electronic processors and one or more digital storage media coupled thereto, and is structured, connected, and programmed so as to (i) receive via the data acquisition system the acquired signals from the multiple sensors, and (ii) to calculate an estimated transverse position of the one or more primary electric arcs within the arc gap, that calculation being based at least in part on longitudinal position of the arc gap, two or more of the magnetic field components measured at two or more corresponding distinct longitudinal positions along the arc furnace, and one or more corresponding sensor positions or calibration parameters, (e) wherein (i) the first conductor comprises an electrode of the arc furnace, (ii) the second conductor comprises an ingot formed within the arc furnace, and (iii) the arc furnace is arranged so that the arc gap moves longitudinally through the chamber as the input current flows during a melt period and causes the electrode to melt and shrink and the ingot to grow.

2. The apparatus of claim 1 wherein each sensor of the set is arranged so as to measure magnetic field components in three spatial dimensions.

3. The apparatus of claim 1 wherein the calculation is based at least in part on magnitude of the input electric current or the primary electric current.

4. The apparatus of claim 1 wherein the one or more corresponding calibration parameters for each sensor are derived from calculations, at multiple distinct transverse positions and at multiple distinct longitudinal positions of a simulated arc gap, of magnetic field components at the corresponding sensor position arising from a simulated input current flowing in a single simulated primary electrical arc, so that for one or more of the multiple sensors the corresponding one or more calibration parameters vary with the longitudinal position of the arc gap.

5. The apparatus of claim 4 wherein one or more calculations include corrections for magnetic field components arising from external conductors carrying the primary current into the current-containing volume or carrying a return current out of the current-containing volume.

6. The apparatus of claim 4 wherein one or more calculations include measured directional corrections to the orientations of the measured magnetic field components for each sensor.

7. The apparatus of claim 4 wherein one or more calculations include measured corrections arising from external magnetic fields in which the current-carrying volume is immersed.

8. The apparatus of claim 1 wherein the multiple sensor positions include two or more rings of sensor positions, wherein each ring includes multiple sensor positions arranged at substantially the same longitudinal position along the current-containing volume and at multiple distinct circumferential positions around the lateral periphery of the current-containing volume.

9. The apparatus of claim 8 wherein the multiple sensor positions include three or more of the rings of sensor positions.

10. The apparatus of claim 8 wherein those sensors positioned at corresponding sensor positions of the two or more rings are arranged so as to measure magnetic field components in two substantially transverse dimensions.

11. The apparatus of claim 8 wherein the multiple sensor positions include one or more sensor positions that are positioned at corresponding longitudinal positions along the current-containing volume that differ from the corresponding longitudinal positions of the two or more rings of sensor positions.

12. The apparatus of claim 8 wherein the estimated transverse position of the one or more primary electric arcs is a weighted average of estimated arc transverse positions calculated for each ring using measured field components from sensors at corresponding sensor positions of only that ring, and the estimated arc transverse positions for each ring are weighted according to a corresponding longitudinal distance between that ring and the estimated longitudinal position of the arc gap, with a corresponding weight factor decreasing with increasing distance between the corresponding ring and the estimated arc gap position.

13. The apparatus of claim 1 wherein two or more of the multiple sensors are arranged so as to measure a magnetic field component in a substantially longitudinal dimension, and the computer system is structured, connected, and programmed so as to recognize one or more sets of measured magnetic field magnitudes or longitudinal components that are indicative of a secondary electric current flowing in a predominantly transverse direction as a secondary electric arc between the first or second conductor and the chamber, that recognition being based at least in part on the magnitude of the input current, an estimated longitudinal position of the arc gap, and two or more of the measured longitudinal magnetic field components along with one or more corresponding sensor positions or calibration parameters.

14. The apparatus of claim 13, wherein the computer system is structured, connected, and programmed so as to calculate an estimated magnitude of the secondary electric current or an estimated position of the secondary electric arc, that calculation being based at least in part on the magnitude of the input current, an estimated longitudinal position of the arc gap, and two or more of the measured longitudinal magnetic field components along with one or more corresponding sensor positions or calibration parameters.

15. The apparatus of claim 13 wherein, with no secondary current flowing, the input current is substantially equal to the primary current.

16. The apparatus of claim 13 wherein, with one or more secondary electric arcs present, the input current is substantially equal to a sum of the primary and secondary currents.

17. The apparatus of claim 1 wherein the computer system is structured, connected, and programmed so as to calculate an estimated arc gap longitudinal position that changes with melt time as the input current flows during the melt period.

18. The apparatus of claim 17 wherein the longitudinal position of one or more selected sensors that register a maximum measured magnetic field magnitude, with respect to melt time as the input current flows during the melt period, is used to estimate longitudinal position of the arc gap at the melt time when the selected sensors register that maximum measured magnetic field magnitude.

19. The apparatus of claim 18 wherein the selected sensors are arranged in a ring around the periphery of the current-carrying volume at a common longitudinal position.

20. The apparatus of claim 17 wherein the longitudinal position of one or more selected sensors that register a minimum measured magnetic field longitudinal component, with respect to melt time as the input current flows during the melt period, is used to estimate longitudinal position of the arc gap at the melt time when the selected sensors register that minimum measured magnetic field longitudinal component.

21. The apparatus of claim 20 wherein the selected sensors are arranged in a ring around the periphery of the current-carrying volume at a common longitudinal position.

22. The apparatus of claim 17 wherein (i) the electrode includes one or more weldments at known longitudinal positions that produce a recognizable alteration of one or more magnetic field components as the electrode melts and the arc gap passes each weldment, (ii) the computer system is structured, connected, and programmed so as to recognize the alteration detected by one or more of the sensors, and (iii) a longitudinal position of corresponding weldment of the electrode is used to estimate the longitudinal position of the arc gap at a melt time when the alteration occurs.

23. The apparatus of claim 17 wherein the computer system is structured, connected, and programmed so as to calculate an estimated arc gap longitudinal position as a function of time as an interpolation between arc gap positions estimated by weldment position, by minimum longitudinal field component detection, or by maximum field magnitude detection.

24. The apparatus of claim 17 wherein the arc gap longitudinal position is estimated based at least in part on size, shape, density, and weight of the first longitudinal electrical conductor, and duration and magnitude of the primary current flow.

25. An apparatus for estimating a location of an electric arc, the apparatus comprising:
   (a) a chamber that is structurally arranged so as to enclose a current-containing volume, define a lateral periphery of the current-containing volume, and enclose first and second longitudinal electrical conductors positioned end-to-end within the chamber separated by an arc gap, the chamber being connected so as to enable an input electric current to flow into the current-containing volume, and at least a portion of the input current to flow in a predominantly longitudinal direction as a primary electric current (i) through at least portions of the first and second longitudinal electrical conductors and (ii) as one or more primary electric arcs that span the arc gap and that are movable in two transverse dimensions within the arc gap between the first and second conductors;
   (b) a set of multiple magnetic field sensors that are arranged around the lateral periphery of the current-containing volume with each sensor of the set positioned at a corresponding one of multiple distinct sensor positions, wherein the multiple sensor positions are located outside the chamber and arranged among two or more distinct longitudinal positions along the current-containing volume and among two or more distinct circumferential positions around the lateral periphery of the current-containing volume, and wherein each sensor of the set is arranged so as to measure magnetic field components in two or more spatial dimensions and is characterized by one or more corresponding calibration parameters;
   (c) a data acquisition system that is structured and connected so as to acquire signals from the multiple sensors indicative of the corresponding measured magnetic field components; and
   (d) a computer system that comprises one or more electronic processors and one or more digital storage media coupled thereto, and is structured, connected, and programmed so as to (i) receive via the data acquisition system the acquired signals from the multiple sensors, and (ii) to calculate an estimated transverse position of the one or more primary electric arcs within the arc gap, that calculation being based at least in part on longitudinal position of the arc gap, and two or more of the measured magnetic field components along with one or more corresponding sensor positions or calibration parameters,
   (e) wherein the one or more corresponding calibration parameters for each sensor are derived from calculations, at multiple distinct transverse positions and at multiple distinct longitudinal positions of a simulated arc gap, of magnetic field components at the corresponding sensor position arising from a simulated input current flowing in a single simulated primary electrical arc, so that for one or more of the multiple sensors the corresponding one or more calibration parameters vary with the longitudinal position of the arc gap.

26. The apparatus of claim 25 wherein one or more calculations include corrections for magnetic field components arising from external conductors carrying the primary current into the current-containing volume or carrying a return current out of the current-containing volume.

27. The apparatus of claim 25 wherein one or more calculations include measured directional corrections to the orientations of the measured magnetic field components for each sensor.

28. The apparatus of claim 25 wherein one or more calculations include measured corrections arising from external magnetic fields in which the current-carrying volume is immersed.

29. An apparatus for estimating a location of an electric arc, the apparatus comprising:
   (a) a chamber that is structurally arranged so as to enclose a current-containing volume, define a lateral periphery of the current-containing volume, and enclose first and second longitudinal electrical conductors positioned end-to-end within the chamber separated by an arc gap, the chamber being connected so as to enable an input electric current to flow into the current-containing volume, and at least a portion of the input current to flow in a predominantly longitudinal direction as a primary electric current (i) through at least portions of the first and second longitudinal electrical conductors and (ii) as one or more primary electric arcs that span the arc gap and that are movable in two transverse dimensions within the arc gap between the first and second conductors;
   (b) a set of multiple magnetic field sensors that are arranged around the lateral periphery of the current-containing volume with each sensor of the set positioned at a corresponding one of multiple distinct sensor positions, wherein the multiple sensor positions are located outside the chamber and arranged among two or more distinct longitudinal positions along the current-containing volume and among two or more distinct circumferential positions around the lateral periphery of the current-containing volume, and wherein each sensor of the set is arranged so as to measure magnetic field components in two or more spatial dimensions and is characterized by one or more corresponding calibration parameters;

(c) a data acquisition system that is structured and connected so as to acquire signals from the multiple sensors indicative of the corresponding measured magnetic field components; and (d) a computer system that comprises one or more electronic processors and one or more digital storage media coupled thereto, and is structured, connected, and programmed so as to (i) receive via the data acquisition system the acquired signals from the multiple sensors, and (ii) to calculate an estimated transverse position of the one or more primary electric arcs within the arc gap, that calculation being based at least in part on longitudinal position of the arc gap, and two or more of the measured magnetic field components along with one or more corresponding sensor positions or calibration parameters, wherein:

(e) the multiple sensor positions include two or more rings of sensor positions, wherein each ring includes multiple sensor positions arranged at substantially the same longitudinal position along the current-containing volume and at multiple distinct circumferential positions around the lateral periphery of the current-containing volume; and (f) the estimated transverse position of the one or more primary electric arcs is a weighted average of estimated arc transverse positions calculated for each ring using measured field components from sensors at corresponding sensor positions of only that ring, and the estimated arc transverse positions for each ring are weighted according to a corresponding longitudinal distance between that ring and the estimated longitudinal position of the arc gap, with a corresponding weight factor decreasing with increasing distance between the corresponding ring and the estimated arc gap position.

30. An apparatus for estimating a location of an electric arc, the apparatus comprising:
(a) a chamber that is structurally arranged so as to enclose a current-containing volume, define a lateral periphery of the current-containing volume, and enclose first and second longitudinal electrical conductors positioned end-to-end within the chamber separated by an arc gap, the chamber being connected so as to enable an input electric current to flow into the current-containing volume, and at least a portion of the input current to flow in a predominantly longitudinal direction as a primary electric current (i) through at least portions of the first and second longitudinal electrical conductors and (ii) as one or more primary electric arcs that span the arc gap and that are movable in two transverse dimensions within the arc gap between the first and second conductors;
(b) a set of multiple magnetic field sensors that are arranged around the lateral periphery of the current-containing volume with each sensor of the set positioned at a corresponding one of multiple distinct sensor positions, wherein the multiple sensor positions are located outside the chamber and arranged among two or more distinct longitudinal positions along the current-containing volume and among two or more distinct circumferential positions around the lateral periphery of the current-containing volume, and wherein each sensor of the set is arranged so as to measure magnetic field components in two or more spatial dimensions and is characterized by one or more corresponding calibration parameters;

(c) a data acquisition system that is structured and connected so as to acquire signals from the multiple sensors indicative of the corresponding measured magnetic field components; and (d) a computer system that comprises one or more electronic processors and one or more digital storage media coupled thereto, and is structured, connected, and programmed so as to (i) receive via the data acquisition system the acquired signals from the multiple sensors, and (ii) to calculate an estimated transverse position of the one or more primary electric arcs within the arc gap, that calculation being based at least in part on longitudinal position of the arc gap, and two or more of the measured magnetic field components along with one or more corresponding sensor positions or calibration parameters, (e) wherein two or more of the multiple sensors are arranged so as to measure a magnetic field component in a substantially longitudinal dimension, and the computer system is structured, connected, and programmed so as to recognize one or more sets of measured magnetic field magnitudes or longitudinal components that are indicative of a secondary electric current flowing in a predominantly transverse direction as a secondary electric arc between the first or second conductor and the chamber, that recognition being based at least in part on the magnitude of the input current, an estimated longitudinal position of the arc gap, and two or more of the measured longitudinal magnetic field components along with one or more corresponding sensor positions or calibration parameters.

31. The apparatus of claim 30, wherein the computer system is structured, connected, and programmed so as to calculate an estimated magnitude of the secondary electric current or an estimated position of the secondary electric arc, that calculation being based at least in part on the magnitude of the input current, an estimated longitudinal position of the arc gap, and two or more of the measured longitudinal magnetic field components along with one or more corresponding sensor positions or calibration parameters.

32. The apparatus of claim 30 wherein, with no secondary current flowing, the input current is substantially equal to the primary current.

33. The apparatus of claim 30 wherein, with one or more secondary electric arcs present, the input current is substantially equal to a sum of the primary and secondary currents.

34. A method, for estimating transverse position of one or more primary electric arcs as a function of longitudinal position of an arc gap moving longitudinally within a chamber of an electric arc furnace during a melt period, the method comprising:
(A) applying an input electric current that flows into the arc furnace so that at least a portion of the input current flows in a predominantly longitudinal direction as a primary electric current (i) through at least portions of first and second longitudinal electrical conductors positioned end-to-end within the chamber and separated by the arc gap, and (ii) as the one or more primary electric arcs spanning the arc gap and movable in two transverse dimensions within the arc gap between the first and second conductors;
(B) measuring magnetic field components in two or more spatial dimensions, using a set of multiple magnetic field sensors that are arranged around a lateral periphery, defined by the chamber, of a current-containing volume enclosed by the chamber, wherein (i) each sensor is positioned at a corresponding one of multiple sensor positions arranged around the lateral periphery of the current-containing volume outside the chamber, (ii) the multiple sensor positions are arranged among two or more distinct longitudinal positions along the current-carrying volume and among two or more distinct circumferential positions around the lateral periphery of the current-carrying volume, and (iii) each sensor is characterized by one or more corresponding calibration parameters;

(C) acquiring from the multiple sensors, using a data acquisition system structured and connected therefor, signals indicative of the corresponding measured magnetic field components; and (D) receiving via the data acquisition system, at a computer system that is structured, connected, and programmed therefor and comprises one or more electronic processor and one or more digital storage media, the signals acquired from the multiple sensors for each one of multiple melt times within the melt period; and (E) calculating using the computer system, for each one of the multiple melt times during the melt period, a corresponding estimated transverse position of the one or more primary electric arcs within the arc gap, that calculation being based at least in part on the longitudinal position of the arc gap at the corresponding melt time, two or more of the magnetic field components measured at the corresponding melt time at two or more corresponding distinct longitudinal positions along the arc furnace, and one or more corresponding sensor positions or calibration parameters, (F) wherein (i) the first conductor comprises an electrode of the arc furnace, (ii) the second conductor comprises an ingot formed within the arc furnace, and (iii) the arc furnace is arranged so that the arc gap moves longitudinally through the chamber as the input current flows during a melt period and causes the electrode to melt and shrink and the ingot to grow.

* * * * *